US012714669B2

(12) United States Patent
Barenholz et al.

(10) Patent No.: US 12,714,669 B2
(45) Date of Patent: Aug. 25, 2026

(54) LIPOSOMAL FORMULATIONS COMPRISING AT1 RECEPTOR BLOCKERS AND USES THEREOF

(71) Applicant: YISSUM RESEARCH DEVELOPMENT COMPANY OF THE HEBREW UNIVERSITY OF JERUSALEM LTD, Jerusalem (IL)

(72) Inventors: Yechezkel Barenholz, Jerusalem (IL); Ahuva Cern, Modiin (IL); Amiram Goldblum, Tel Aviv (IL)

(73) Assignee: YISSUM RESEARCH DEVELOPMENT COMPANY OF THE HEBREW UNIVERSITY OF JERUSALEM LTD, Jerusalem (IL)

( * ) Notice: Subject to any disclaimer, the term of this patent is extended or adjusted under 35 U.S.C. 154(b) by 895 days.

(21) Appl. No.: 17/793,254

(22) PCT Filed: Mar. 25, 2021

(86) PCT No.: PCT/IL2021/050336

§ 371 (c)(1),
(2) Date: Jul. 15, 2022

(87) PCT Pub. No.: WO2021/191907

PCT Pub. Date: Sep. 30, 2021

(65) Prior Publication Data

US 2023/0129331 A1 Apr. 27, 2023

Related U.S. Application Data

(60) Provisional application No. 62/994,688, filed on Mar. 25, 2020.

(51) Int. Cl.

| | |
|---|---|
| ***A61K 47/54*** | (2017.01) |
| ***A61K 9/127*** | (2006.01) |
| ***C07D 257/04*** | (2006.01) |
| ***C07D 403/10*** | (2006.01) |

(52) U.S. Cl.

CPC ............ *A61K 9/127* (2013.01); *A61K 47/544* (2017.08); *C07D 257/04* (2013.01); *C07D 403/10* (2013.01)

(58) Field of Classification Search

None

See application file for complete search history.

(56) References Cited

U.S. PATENT DOCUMENTS 8,293,723 B2 * 10/2012 Sinisterra Millan ..... A61K 9/19 514/397
2017/0027869 A1 * 2/2017 Barenholz .......... A61K 47/6951

FOREIGN PATENT DOCUMENTS

| | | | | |
|---|---|---|---|---|
| CN | 101797230 A | | 8/2010 | |
| CN | 101810580 A | | 8/2010 | |
| CN | 103040777 A | | 4/2013 | |
| CN | 106659795 A | | 5/2017 | |
| WO | 2015155773 A1 | | 10/2015 | |
| WO | WO-2016013031 A1 | * | 1/2016 | ............. A61K 31/41 |

OTHER PUBLICATIONS

Chauhan , et al., "Reprogramming the microenvironment with tumor- selective angiotensin blockers enhances cancer Immunotherapy", Proc. Natl. Acad. Sci. U. S. A. 166, vol. 116, No. 22, Apr. 2019, pp. 10674-10680, doi:10.1073/pnas.1819889116.

Golder , et al., "Reduction of liver fibrosis by rationally designed macromolecular telmisartan prodrugs", Nature Biomedical Engineering, vol. 2, Nov. 2018, pp. 822-830, doi:10.1038/s41551-018-0279-x.

Xia , et al., "Losartan loaded liposomes improve the antitumor efficacy of liposomal paclitaxel modified with pH sensitive peptides by inhibition of collagen in breast cancer", Pharmaceutical Development and Technology, vol. 23, No. 1, 2018, pp. 13-21, doi: 10.1080/10837450.2016.1265553.

Zhu , et al., "Inhibition of tumor-promoting stroma to enforce subsequently targeting AT1R on tumor cells by pathological inspired micelles", Biomaterials 161, Jan. 2018, pp. 33-46, doi:10.1016/j.biomaterials.2018.01.023.

* cited by examiner

*Primary Examiner* — Celeste A Roney
(74) *Attorney, Agent, or Firm* — Ballard Spahr LLP

(57) ABSTRACT

The present disclosure provides liposomal formulations comprising a lipid membrane comprising at least one liposome forming phospholipid and a sterol; and an intraliposomal aqueous compartment encapsulating at least one ATI receptor blocker (ARB) and a pH-dependent ionizable anion; with the liposomes having an effect upon administration to a subject in need of said effect, without causing a reduction in mean blood pressure of said subject of more than 50% as compared to the administration of the same amount of ARB in free form. The liposomes can be for systemic administration, e.g. by injection or for pulmonary administration, e.g. by inhalation.

18 Claims, 6 Drawing Sheets

LIPOSOMAL FORMULATIONS COMPRISING AT1 RECEPTOR BLOCKERS AND USES THEREOF

TECHNOLOGICAL FIELD

The present disclosure concerns drug delivery systems and in particular, liposomal drug delivery systems

BACKGROUND ART

References considered to be relevant as background to the presently disclosed subject matter are listed below:

V. P. Chauhan, I. X. Chen, R. Tong, M. R. Ng, J. D. Martin, K. Naxerova, M. W. Wu, P. Huang, Y. Boucher, D. S. Kohane, R. Langer, R. K. Jain, Reprogramming the microenvironment with tumorselective angiotensin blockers enhances cancer immunotherapy, Proc. Natl. Acad. Sci. U.S.A. 166 (2019) 10674-10680. doi: 10.1073/pnas.1819889116

Y. Zhu, L. Wen, S. Shao, Y. Tan, T. Meng, X. Yang, Y. Liu, X. Liu, H. Yuan, F. Hu, Inhibition of tumor-promoting stroma to enforce subsequently targeting AT1R on tumor cells by pathological inspired micelles, Biomaterials. 161 (2018) 33-46. doi:10.1016/j.biomaterials.2018.01.023

M. R. Golder, J. Liu, J. N. Andersen, M. V. Shipitsin, F. Vohidov, H. V. T. Nguyen, D. C. Ehrlich, S. J. Huh, B. Vangamudi, K. D. Economides, A. M. Neenan, J. C. Ackley, J. Baddour, S. Paramasivan, S. W. Brady, E. J. Held, L. A. Reiter, J. K. Saucier-Sawyer, P. W. Kopesky, D. E. Chickering, P. Blume-Jensen, J. A. Johnson, Reduction of liver fibrosis by rationally designed macromolecular telmisartan prodrugs, Nat. Biomed. Eng. 2 (2018) 822-830. doi:10.1038/s41551-018-0279-x T. Xia, Q. He, K. Shi, Y. Wang, Q. Yu, L. Zhang, Q. Zhang, H. Gao, L. Ma, J. Liu, Losartan loaded liposomes improve the antitumor efficacy of liposomal paclitaxel modified with pH sensitive peptides by inhibition of collagen in breast cancer, Pharm. Dev. Technol. 23 (2018) 13-21. doi:10.1080/10837450.2016.1265553

International patent application publication no. WO15155773

Acknowledgement of the above references herein is not to be inferred as meaning that these are in any way relevant to the patentability of the presently disclosed subject matter.

BACKGROUND

Angiotensin II (Ang II) is the major effector peptide of the renin—angiotensin system (RAS). Ang II binds to two receptor subtypes, Ang II type 1 and type 2 (AT1 and AT2) receptors, which are members of the G protein-coupled receptor superfamily (GPCRs). AT1 receptor blockers (ARBs) are highly selective for the AT1 receptor and block the deleterious effects of Ang II, such as vasoconstriction, aldosterone release, retention of sodium and water, sympathetic nerve activation and cell proliferation and are used in the clinic as anti-hypertensive drugs. However, ACE and AT1R have important roles in cancer development: (1) Cell migration, invasion and metastasis; (2) Differentiation of fibroblasts due to TGFβ-mediated induction of extracellular matrix proteins resulting in increased mechanical stress; (3) Effects on endothelial cells of the tumor vasculature contribute to tumor hypoxia with increased vascular constriction; and (4) Secretion of cytokines which in turn cause M2-macrophage polarization, suppression of the cytolytic activity of CD8+ T cells. ARB's has therefore the potential to affect these activities.

ARB's may also improve the activity of Immune checkpoint inhibition (ICI). Local RAS in cancer microenvironments was found to have profound impact, inducing immunosuppression by enhancing the immunosuppressive activities of macrophages, myeloid-derived suppressor cell (MDSC), and CAF. This effect was reversed by angiotensin receptor blocker (ARB) treatment.

ARB's may also be used as a potential treatment for coronavirus infections. The coronavirus S (spike) protein utilizes ACE2 as a receptor for host cell entry. The S protein binds the catalytic domain of ACE2 with high affinity. This binding triggers a conformational change in the S protein of the coronavirus, allowing for proteolytic digestion by host cell proteases (TMPRSS2) [Hoffmann M, Kleine-Weber H, Schroeder S, Kruger N, Herrler T, Erichsen S, et al. SARS-CoV-2 Cell Entry Depends on ACE2 and TMPRSS2 and Is Blocked by a Clinically Proven Protease Inhibitor. Cell. 2020; 181(2):271-80 e8. Epub 2020/03/07. https://doi.org/10.1016/j.ce11.2020.02.052 PMID: 32142651; PubMed Central PMCID: PMC7102627]. It has been demonstrated that the binding of the coronavirus spike protein to ACE2, its cellular binding site, leads to ACE2 downregulation, which in turn results in excessive production of angiotensin by the related enzyme ACE, while less ACE2 is capable of converting it to the vasodilator heptapeptide angiotensin (1-7). This in turn contributes to lung injury, as angiotensin II binding to AT receptor results in increased pulmonary vascular permeability, thereby mediating increased lung pathology.

Using ARB's two complementary mechanisms occur: blocking the excessive angiotensin-mediated AT receptor activation caused by the viral infection, as well as upregulating ACE2, thereby reducing angiotensin production by ACE and increasing the production of the vasodilator angiotensin 1-7 [D. Gurwitz, Angiotensin receptor blockers as tentative SARS-CoV-2 therapeutics., Drug Dev. Res. (2020) 2-5. doi:10.1002/ddr.21656]. Thus, ARB's administration is therapeutic approach to the COVID-19 infection.

In summary, ARB's demonstrate wide and diverse actions including the inhibition of angiogenesis, affecting the TME and changing of the immune milieu.

However, ARB's clinical use in cancer therapy is limited by systemic adverse effects such as hypotension. Selective targeting of ARBs to the tumors is required in order to avoid or minimize unwanted systemic physiological effects.

V. P. Chauhan et al. (2019) describe a nano-formulation consisting of valsartan bound to pH-sensitive polymer in the form of nano, thus creating a nano-ARB, which abrogates the blood-pressure reducing effect of valsartan while increasing the extent of TME normalization.

Y. Zhu, et al. (2018) describe a nano-formulation of telmisartan (telmisartan being an angiotensin II type 1 (AT1) receptor antagonist) chitosan-based glycolipid micelles.

M. R. Golder et al. (2018) describe a nano-formulation of telmisartan brush-arm star polymer.

T. Xia, et al. (2018) describe liposomal Losartan (a selective angiotensin II type 1 (AT1) receptor antagonist), the liposomes being based on Soy phosphatidylcholine (Soy-PC) which are very leaky.

Finally, liposomal formulations for systemic administration are described in WO 15/155773.

General Description

The present disclosure is based on the development of nano-formulations that overcome obstacles associated with systemic delivery of ARBs. This was achieved by the development of injectable PEGylated nano-liposomal formulations or inhalable nano-liposomal formulations loaded with at least one ARBs.

A unique feature of the nano-liposomal formulations encapsulating ARBs is that they lack the side effect of ARBs of reducing blood pressure (e.g. when delivered in free form).

The disclosed formulations can be effective in treating cancer, diabetic retinopathy (which is the leading cause of blindness in working aged people) as well as in other indications which require systemic delivery of ARBs, as further discussed hereinbelow. Such liposomes are preferably suitable for administration by injection.

In some other aspects, the disclosed formulations can be effective in treating viral infections, particularly of the respiratory tract. According to this aspect, the liposomes are preferably suitable for administration by inhalation, as further discussed below.

Thus, in accordance with a first aspect referred to herein as the "injectable liposomes aspect", there are disclosed herein liposomes comprising a lipid membrane comprising at least one liposome forming phospholipid and a sterol; and an intraliposomal aqueous compartment encapsulating at least one AT1 receptor blocker (ARB) and a pH-dependent ionizable anion;

wherein

- the weight ratio between said at least one liposome forming phospholipid and said sterol being between 3:1 and 2:1;
- the liposomes have an ARB to phospholipid molar ratio within the range of 0.02 to 1.0 (the ratio also taking into consideration a lipopolymer, if the lipid membrane includes a lipopolymer); and
- said liposomes have an effect upon systemic administration thereof to a subject in need of said effect, without causing a reduction in mean blood pressure in said subject of more than 50% as compared to systemic administration of the same ARB in free form.

The disclosed injectable liposomes have shown to fulfill several prerequisites for clinically viable formulation based on liposomes for systemic delivery. One concerns sufficient level of drug loading; a second is to maintain the ARB in liposomes while circulating in the blood; a third is to release the drug at the target site at a rate and level that is sufficient to result in a desired therapeutic efficacy; and a fourth it to achieve a pharmaceutically accepted product in terms of shelf-life stability.

Also disclosed herein, in accordance with a second aspect referred to herein as the "inhalable liposomes aspect", there are disclosed liposomes comprising a lipid membrane comprising at least one liposome forming phospholipid and a sterol; and an intraliposomal aqueous compartment encapsulating at least one AT1 receptor blocker (ARB); wherein said liposomes have an average size of between 50 nm and 600 nm and wherein said liposomes have a local effect in a subject's respiratory tract upon inhalation thereof, without causing a reduction in mean blood pressure in said subject of more than 50% as compared to inhalation of the same amount of ARB in free form.

Also disclosed herein are formulations comprising the liposomes, the formulation being suitable for systemic administration, when referring to the injectable liposomes, or suitable for administration by inhalation, when referring to the inhalable liposomes; and methods of treatment comprising administering to a subject in need of said treatment the liposomes disclosed herein.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION

Figure 1:
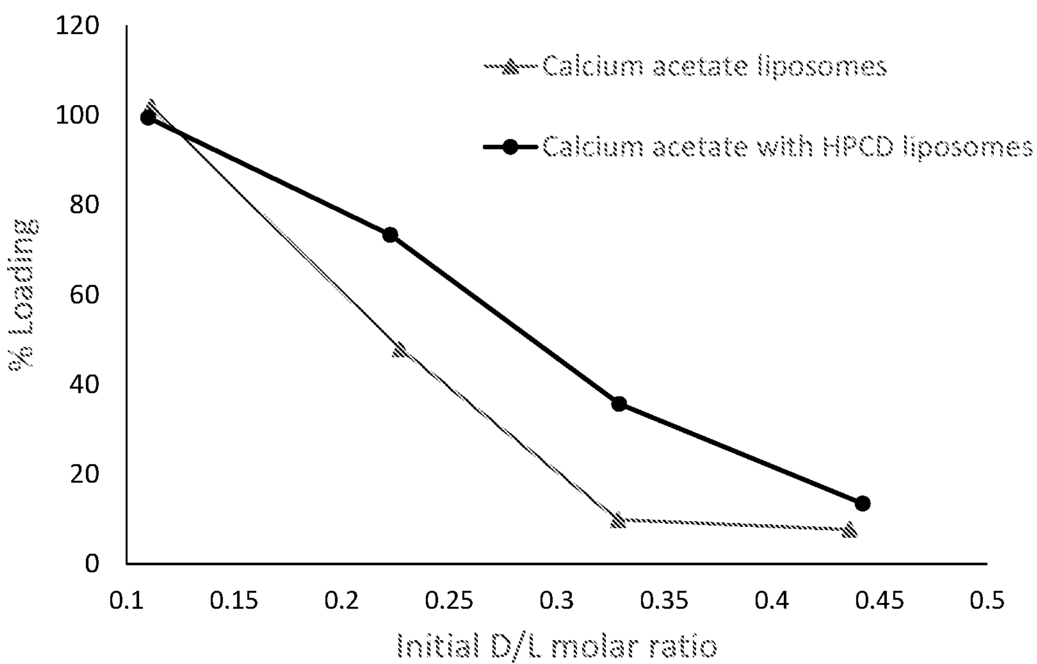
FIG. 1 is a graph showing percent % loading of valsartan into liposomes following 10 min of incubation at different D/L molar ratios.

The present disclosure is based on the development of several formulations comprising injectable liposomes encapsulating AT1 receptor blockers (ARBs). In some examples, the injectable liposomes developed are PEGylated nano-liposomes containing either valsartan or candesartan. These liposomes, and specifically the nano-liposomes containing valsartan were tested for their in vivo lack of effect on blood pressure to ensure the ability of the formulation to concentrate in tumors and avoid any effect on systemic blood pressure.

The non-limiting examples provided herein demonstrate high loading for valsartan and candesartan, long term stability and sustained release in serum.

When referring to Valsartan, it is to be understood as referring to the compound of (2S)-3-methyl-2-[pentanoyl-[[4-[2-(2H-tetrazol-5-yl)phenyl]phenyl]methyl]amino]butanoic acid having the Formula I:

Formula I

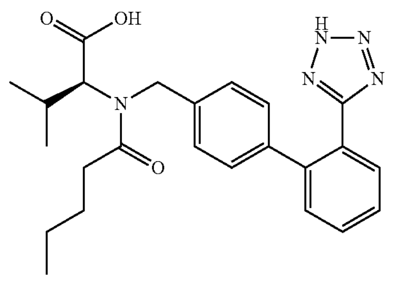

When referring to Candesartan, it is to be understood as referring to the compound of 2-ethoxy-3-[[4-[2-(2H-tetrazol-5-yl)phenyl]phenyl]methyl]benzimidazole-4-carboxylic acid, having the Formula II:

Formula II

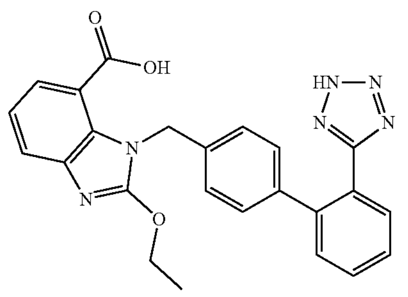

Further, in some examples, the ARB can be the compound 5-(1,1,2,2,2-pentafluoroethyl)-2-propyl-3-[[4-[2-(2H-tetrazol-5-yl)phenyl]phenyl]methyl]imidazole-4-carboxylic acid of Formula III:

Formula III

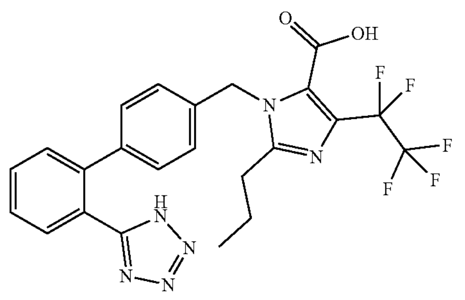

Specifically, without being limited thereto, Valsartan showed high loading efficiency into PEGylated nano-liposomes exhibiting trans-membrane calcium acetate gradient with and without 15 and 25% HPCD in their intra-liposome aqueous phase. The Valsartan formulations showed stable loading for at least 15 months at 4° C. (stability study is ongoing). The liposomes were also stable when incubated for 24 hours at 37° C. after dilution in dextrose. The Valsartan formulations containing 15% and 25% HPCD showed that 80-82% of Valsartan remained liposomal after 24 h of incubation in the presence of 50% serum compared to zero-time content (94-96%). However, valsartan liposomes without HPCD retained only 48% of valsartan as liposomal.

Further, without being limited thereto, Candesartan (although not soluble in aqueous media) showed high loading from a dispersion in phosphate buffer into liposomes exhibiting trans-membrane calcium acetate gradient with and without HPCD. Candesartan concentrations of the liposome dispersion reached a maximum of ~3.4 mg/ml. No release was shown for both liposomes containing and lacking HPCD in their intra-liposome aqueous phase in the presence of 50% serum.

The non-limiting examples provided herein also show the effect on mean blood pressure (MBP) in mice for liposomal valsartan (in liposomes containing 15% HPCD) compared to free valsartan. Free valsartan caused reduction in MBP 2 h after injection, while the valsartan liposomal formulation showed no effect on MBP, demonstrating an unexpected advantage using liposomal ARBs.

Based on the present disclosure, there are thus provided, in accordance with the broadest scope, liposomes comprising a lipid membrane comprising at least one liposome forming phospholipid and a sterol, and an intraliposomal aqueous compartment encapsulating at least one AT1 receptor blocker (ARB) and a pH-dependent ionizable anion.

In accordance with the injectable liposomes aspect, there are provided liposomes comprising a lipid membrane comprising at least one liposome forming phospholipid and a sterol; and an intraliposomal aqueous compartment encapsulating at least one AT1 receptor blocker (ARB) and a pH-dependent ionizable anion; wherein the weight ratio between said at least one liposome forming lipid and said sterol being between 3:1 and 2:1;

the liposomes have an ARB to phospholipid molar ratio within the range of 0.02 to 1.0; and said liposomes have an effect upon systemic administration thereof to a subject in need of said effect, without causing a reduction in mean blood pressure of said subject of more than 50% as compared to systemic administration of the same dose of ARB in free form.

Further, in accordance with the inhalable liposomes aspect, there are provided liposomes comprising a lipid membrane comprising at least one liposome forming phospholipid and a sterol; and an intraliposomal aqueous compartment encapsulating at least one AT1 receptor blocker (ARB); wherein said liposomes have an average size of between 50 nm and 600 nm and wherein said liposomes have a local effect in the subject's respiratory tract upon inhalation thereof, without causing a reduction in mean blood pressure in said subject of more than 50% as compared to inhalation of the same amount of ARB in free form.

At times, and in accordance with some examples, the inhalable liposomes have an average size of between 100 nm and 400 nm, at times between 50 nm and 300 nm, at times between 50 nm and 200 nm, at times between 100 nm and 300 nm.

In some examples, the inhalable liposomes have an average size falling within any range between 50 nm and 500 nm.

In some examples, the inhalable liposomes have an average size of about 300 nm.

In the context of the present invention, the term "liposome forming phospholipids" denotes primarily glycerophospholipids or sphingomyelins that form in water into vesicles, such as, but without being limited thereto, liposomes, as further discussed below.

When referring to glycerophospholipids it is to be understood as lipids having a glycerol backbone wherein at least one, preferably two, of the hydroxyl groups at the head group is substituted by one or two of an acyl, alkyl or alkenyl chain, a phosphate group, or combination of any of the above, and/or derivatives of same and may contain a chemically reactive group (such as an amine, acid, ester, aldehyde or alcohol) at the head group, thereby providing the lipid with a polar head group. The sphingomyelins consist of a ceramide unit with a phosphorylcholine moiety attached to position 1 and thus in fact is an N-acyl sphingosine. The phosphocholine moiety in sphingomyelin contributes the polar head group of the sphingomyelin.

In the liposome forming lipids the acyl, alkyl or alkenyl chain is typically between 14 to about 24 carbon atoms in length, and have varying degrees of saturation being fully, partially or non-hydrogenated naturally occurring lipids, semi-synthetic or fully synthetic lipids and the level of saturation may affect rigidity of the liposome thus formed (typically lipids with saturated chains are more rigid than lipids of same chain length in which there are un-saturated chains, especially having cis double bonds).

In some examples, the liposome comprises a single type or a combination of liposome forming lipids.

In some preferred examples, the lipid membrane consists of a single liposome forming lipid.

In some examples, the liposome forming lipid is a phospholipid. When the liposome forming lipid is phospholipid, the amount thereof in the liposome can be determined as organic phosphorous by the modified Bartlett method [Shmeeda H, Even-Chen S, Honen R, Cohen R, Weintraub C, Barenholz Y. 2003. Enzymatic assays for quality control and pharmacokinetics of liposome formulations: comparison with nonenzymatic conventional methodologies. Methods Enzymol 367:272-92].

In some examples, the liposome forming lipid is a choline-type phospholipids such as diacylglycero-phosphocholine (the acyl, alkyl or alkenyl chain being as defined above).

In some other examples, liposome forming lipid is di-lauroyl-sn-glycero-2phosphocholine (DLPC). In some examples, liposome forming lipid is 1,2-dimyristoyl-sn-glycero-3-phosphocholine (DMPC). In some examples, liposome forming lipid is 1,2-dipalmitoyl-sn-glycero-3-phosphocholine (DPPC). In some examples, the liposome forming lipid is 1,2-dipalmitoyl-sn-glycero-3-phosphocholine (DPPC). In some examples, the liposome forming lipid is 1,2-diheptadecanoyl-sn-glycero-3-phosphocholine. In some examples, the liposome forming lipid is 1,2-distearoyl-sn-glycero-3-phosphocholine (DSPC). In some examples, the liposome forming lipid is 1,2-dinonadecanoyl-sn-glycero-3-phosphocholine. In some examples, the liposome forming lipid is 1,2-diarachidoyl-sn-glycero-3-phosphocholine (DBPC). In some examples, the liposome forming lipid is 1,2-dihenarachidoyl-sn-glycero-3-phosphocholine. In some examples, the liposome forming lipid is 1,2-dibehenoyl-sn-glycero-3-phosphocholine 1,2-ditricosanoyl-sn-glycero-3-phosphocholine. In some examples, the liposome forming lipid is 1,2-dilignoceroyl-sn-glycero-3-phosphocholine. In some examples, the liposome forming lipid is 1-myristoyl-2-stearoyl-sn-glycero-3-phosphocholine. In some examples, the liposome forming lipid is 1-palmitoyl-2-stearoyl-sn-glycero-3-phosphocholine (PSPC). In some examples, the liposome forming lipid is 1-stearoyl-2-palmitoyl-sn-glycero-3-phosphocholine (SPPC). In some examples, the liposome forming lipid is 1,2-di-oleoyl-sn-glycero-3-phosphocholine (DOPC) or di-lauroyl-sn-glycero-2phosphocholine (DLPC).

In some examples, the liposome forming phospholipid is an ionizable lipid, such as those described by Buschmann, M. D. et al. [Buschmann, M. D. et al. Nanomaterial Delivery Systems for mRNA Vaccines. Vaccines 2021, 9, 65. https://doi.org/10.3390/vaccines, the content of which is incorporated herein by reference] and having a pKa lower than pH 7. For example, the ionizable phospholipid can be anyone having the structure:

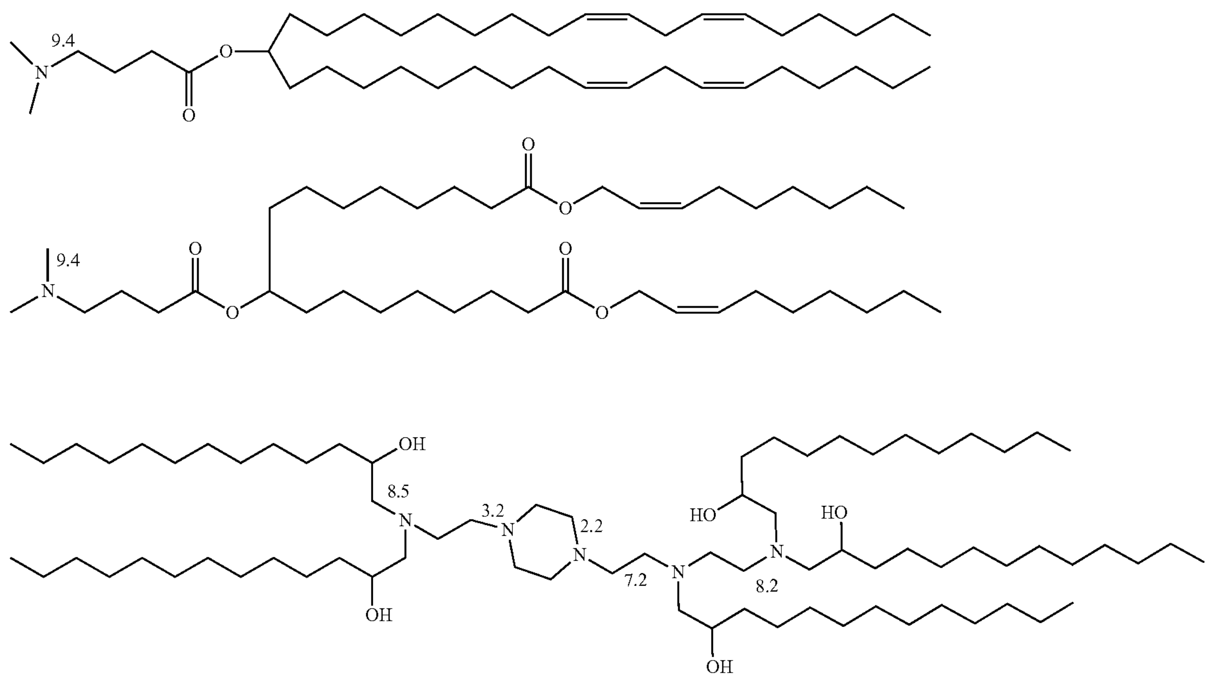

-continued
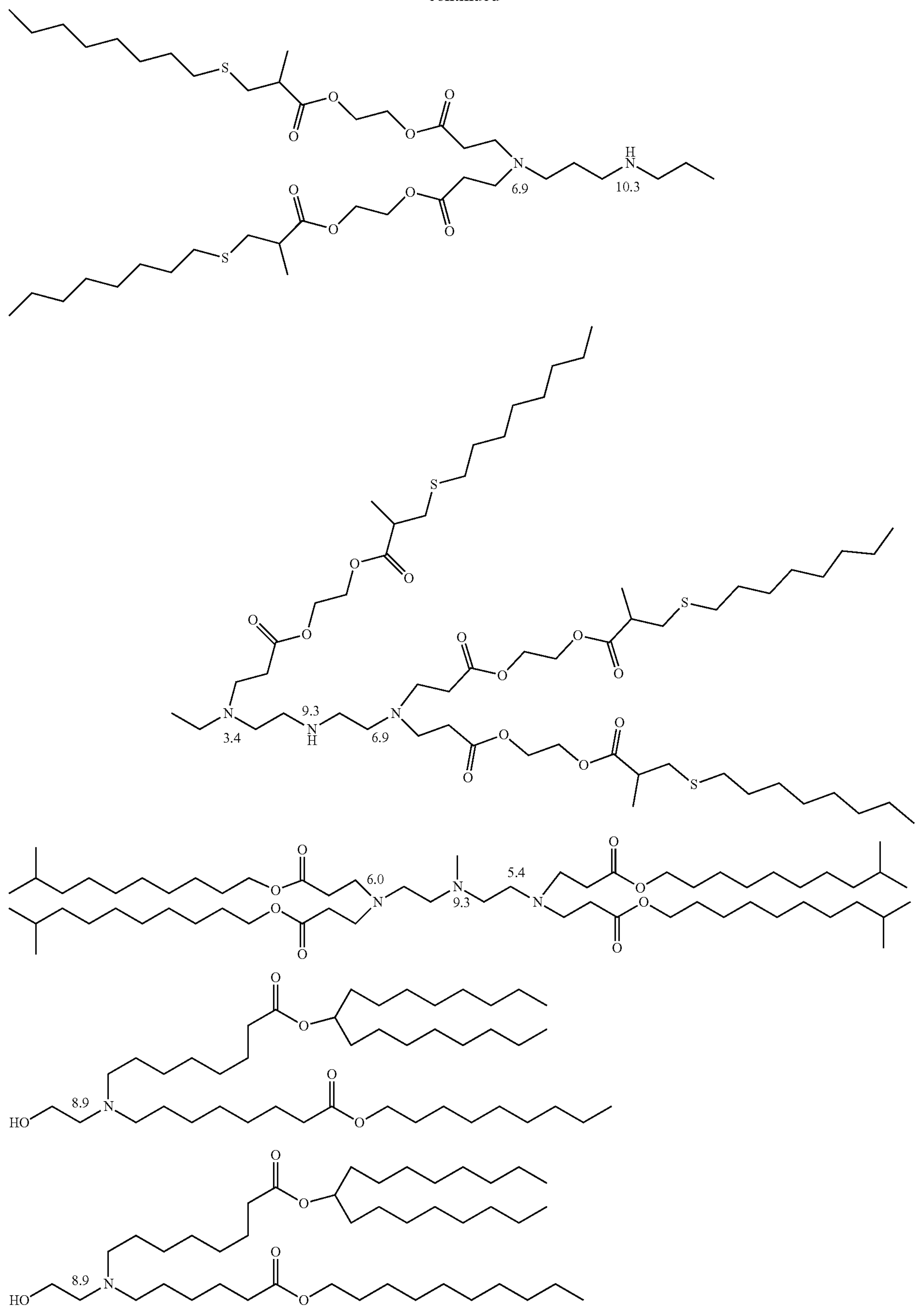

-continued

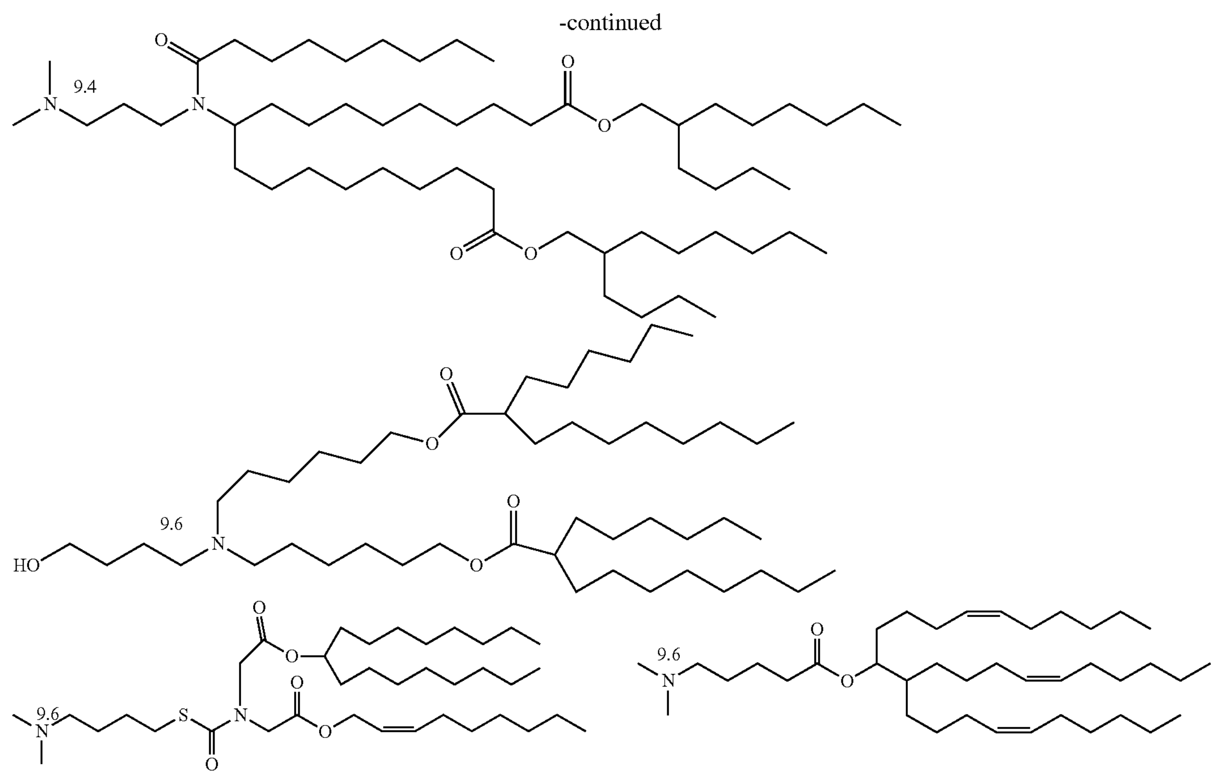

In some examples, the liposome forming phospholipid comprises at least hydrogenated soy phosphatidylcholine (HSPC).

In one preferred embodiment, particularly relating to the injectable liposomes aspect, the liposome forming lipid consists of hydrogenated soy phosphatidylcholine (HSPC), and optionally a lipopolymer as further detailed below.

In some other preferred embodiments, particularly relating to the inhalable liposomes aspect, the liposome forming lipid consists of DPPC.

In some examples the liposome comprises a sterol, such as and at times preferably cholesterol.

In some examples, the liposome comprises a lipopolymer. Lipopolymers comprise lipids modified at their head group with a polymer moiety (PEG) having a molecular weight equal or above 750 Da. The head group may be polar or apolar, to which a large (>750 Da) a flexible hydrophilic polymer is attached. The attachment of the hydrophilic polymer head group to the lipid region may be a covalent or non-covalent attachment, however, is preferably via the formation of a covalent bond (optionally via a linker).

While the lipids modified into lipopolymers may be neutral, negatively charged, as well positively charged, i.e. there is not restriction to a specific (or no) charge. For example the neutral distearoyl glycerol and the negatively charged distearoyl phosphatidylethanolamine, both covalently attached to methoxy poly(ethylene glycol) (mPEG or PEG) of Mw 750, 2000, 5000,or 12000 [Priev A, et al. Langmuir 18, 612-617 (2002); Garbuzenko O., Chem Phys Lipids 135, 117-129(2005); M.C. Woodle and DD Lasic Biochim. Biohys. Acta, 113, 171-199. 1992].

The most commonly used and commercially available lipids derivatized into lipopolymers are those based on phosphatidyl ethanolamine (PE), usually, di stearylphosphatidylethanolamine (DSPE). A specific family of lipopolymers employed by the invention include methoxy PEG-DSPE (with different lengths of PEG chains) in which the PEG polymer is linked to the DSPE primary amino group via a carbamate linkage. The PEG moiety preferably has a molecular weight of the head group is from about 750 Da to about 20,000 Da. More preferably, the molecular weight is from about 750 Da to about 12,000 Da and most preferably between about 1,000 Da to about 5,000 Da. One specific PEG-DSPE employed herein is that wherein PEG has a molecular weight of 2000 Da, designated herein $^{2000}$PEG-DSPE or $^{2k}$PEG-DSPE (M. C. Woodle and DD Lasic Biochim. Biohys. Acta, 113, 171-199. 1992).

One particular embodiment in the context of the present disclosure which relates to the injectable liposomes aspect concerns liposomes comprising at least hydrogenated soybean phosphatidylcholime (HSPC), a lipopolymer of 1,2-distearoyl-sn-glycero-3-phosphoethanolamine-N-[methoxy (polyethylene glycol)-2000] ($^{2k}$PEG-DSPE) and cholesterol.

In some examples, particularly when referring to the injectable liposome aspect, the liposomal membrane comprises between 0.5 mole % to 10 mole % lipopolymer. At times, the liposomal membrane comprises at least 0.5 mole % lipopolymer; at times, at least 1 mole % lipopolymer; at times, at least 2 mole % lipopolymer, at times, at least 3 mole % lipopolymer, at times, at least 4 mole % lipopolymer, at times, at least 5 mole % lipopolymer, at times, at least 6 mole % lipopolymer, at times, at least 7 mole % lipopolymer, at times, at least 8 mole % lipopolymer. At times, the liposomal membrane comprises at most 8 mole % lipopolymer, at times, at most 7 mole % lipopolymer; at most 6 mole % lipopolymer; at most 5 mole % lipopolymer; at most 4 mole % lipopolymer; at most 3 mole % lipopolymer; at most 2 mole % lipopolymer.

In some examples, particularly when referring to the injectable liposome aspect, the lipid membrane comprises hydrogenated soy phosphatidyl choline (HSPC), cholesterol and mPEG-DSPE. One particular molar ratio when using this combination of components comprises a molar ratio of the hydrogenated soy phosphatidyl choline (HSPC), cholesterol and mPEG-DSPE being HSPC:cholesterol:mPEG-DSPE of about 55:40:5.

In the context of the present disclosure, when referring to "pH dependent ionizable anion" it is to be understood as any salt derived anion that is charged under suitable pH conditions. Thus, it is to be understood that the anion may in fact be in a non-ionized form when in the liposome such that when it is in ionized form, it is retained in the liposome and when in non-ion form, it will pass through the lipid membrane and leak out from the intraliposomal core of the liposome. This will depend on the internal pH, i.e. the pH within the intraliposmal compartment. The salt is one having a high solubility (of at least 250 mM), with the anion being one that has a pKa above 3.5 and a logD at pH 7 in the range between about −2.5 and about 1.5, preferably, in the range between about −1.5 and about 1.0. In some examples, the pH-dependent ionizable anion is selected from the group consisting of acetate, benzoate, formate. In some examples, the anion is an organic anion such as choline. In one example, the anion is acetate.

The cation within the salt serves within the liposome as a counter ion to the loaded ARBs. Being a weak amphipathic acid, a suitable counter cation can be an organic as well as inorganic cation. In some examples, the counter cation is selected from the group consisting of calcium, magnesium, and sodium. In some examples the cation is counter to the pH dependent ionizable anion, preferably acetate (which is usually the driving force for the remote loading of the ARBs into the liposomes) that has a very low permeability coefficient, preferably $<10^{-11}$.

In some other examples, the counter cation comprises a cationic polymer. Non-limiting examples of cationic polymers include dextran spermine, dextran spermidine, aminoethyl dextran, trimethyl ammonium dextran, diethylaminoethyl dextran, polyethyleneimine dextran and the like.

In some particular examples, the counter cation is calcium. In some examples, the calcium ion is derived from any one of calcium format, calcium acetate and calcium benzoate.

In some other examples, the counter cation is sodium, e.g. one derived from sodium acetate, sodium format and sodium benzoate.

In some examples, the liposomes comprise calcium acetate or sodium acetate, preferably calcium acetate.

In some examples, the molar ratio between the ion and lipid is between about 0.1 to about 0.5, at times between about 0.2 to 0.4, further at times, the molar ratio is about 0.3±0.05.

With respect to the ARB per se, such as valsartan or candesartan, the amount thereof entrapped in the liposome is specifically important as it is one of the pre-requisite for clinically acceptable liposomal formulation. To assess ARB entrapment, the ARB to lipid ratio is determined and compared to an initial ratio (before encapsulation). To this end, ARB loaded liposomes are commonly purified to remove unencapsulated ARB following ARB loading. Then, the amount of ARB and the amount of lipid in the liposomes is determined by conventional methods. Based on the determined amounts of the ARB and lipid, various parameters are determinable and important to characterize the liposomes: "ARB load" which is the grams or moles of ARB per grams or mole of lipid; and "entrapment efficiency" expressed as the percentage of ARB encapsulated as a function of the initial preload ratio; and "ARB to lipid molar ratio" which is the mole of ARB per mole of lipid following removal of un-encapsulated ARB.

The amount of ARB in the liposomes can be determined using various chromatography techniques. In some examples, the concentration of the ARB compound is determined using a High Performance Liquid Chromatography (HPLC)/UV method. To calculate the intra-liposomal concentration of the ARB one also need the aqueous intra-liposome trapped volume which can be calculated from the intra-liposome calcium concentration (described previously). ARB-liposomal concentration in the formulation is determined by HPLC method. Dividing this concentration by the intraliposomal trapped volume will result in intraliposomal ARB concentration.

In some examples, the ARB load is in the range of 2 and 10 mg/ml of liposome dispersion. In some examples, the ARB load is at least 2 mg/ml; at times, at least 3 mg/ml, at times at least 4 mg/ml, at times at least 5 mg/ml at times at least 6 mg/ml at times at least 7 mg/ml, at times at least 8 mg/ml. In some examples, the ARB load is at most 10 mg/ml, at times, at most 9 mg/ml, at times, at most 8 mg/ml at times, at most 7 mg/ml at times, at most 6 mg/ml at times.

In some more specific examples, the ARB load is in the range of 2 and 5 mg/ml of liposome dispersion.

In some examples, the ARB to phospholipid molar ratio is determined. In this connection, it is noted that when the lipid membrane comprises a lipopolymer, the ARB to phospholipid ratio also takes into consideration the lipopolymer and thus the ARB to phospholipid ratio includes two lipids, the lipopolymer and at least one other PC.

In some examples, the ARB/phospholipid molar ratio is between 0.0.02 and 1.0; at times, at least 0.03, at times at least 0.04, at times, at least 0.05 at least 0.06, or at least 0.07, or at least 0.08, or at least 0.09, or at least 0.1, or at least 0.15, or at least 0.2, or at least 0.25, or at least 0.3, or at least 0.35, or at least 0.4, or at least 0.45, or at least 0.5, or at least 0.55, or at least 0.6, or at least 0.65, or at least 0.7, or at least 0.75, or at least 0.8, or at least 0.85, or at least 0.9, or at least 0.95, or at least 1.0. In some examples, the molar ratio is at most 1.0, or at most 0.9, or at most 0.8, or at most 0.7 or at most 0.6, or at most 0.5, or at most 0.4, or at most 0.3.

In some examples, ARB to phospholipid molar ratio is between 0.1 and 0.5.

In some examples, ARB to phospholipid molar ratio is between 0.2 and 0.4.

In some examples, the liposomes, particularly those of the injectable liposome aspect, comprise at least one cyclodextrin (CD) compound in the intraliposomal compartment.

CD compounds are recognized as cyclic oligosaccharides consisting of (α-1,4)-linked α-D-glucopyranose units and contain a lipophilic central cavity and hydrophilic outer surface. In the context of the present disclosure, the CD can be a naturally occurring CD, as well as derivatives of the naturally occurring CDs. Natural CD include the α-, β-, or γ-cyclodextrin (αCD, βCD or γCD) consisting of six, seven and eight glucopyranose units, respectively. When referring to derivatives of the natural CD it is to be understood as any cyclic oligosaccharides consisting of (α-1,4)-linked α-D-glucopyranose units having a lipophilic central cavity and hydrophilic outer surface.

In some examples, the CD is 2-hydroxypropyl-β-cyclodextrin (HPβCD).

In some examples, the CD is 2-hydroxypropyl-γ-cyclodextrin (HPγCD).

In some examples, the CD is Solfobutyl ether (SBE) cyclodextrin.

In one preferred example, the CD is HPβCD.

The liposomes disclosed herein comprise an amount of CD sufficient to allow stability of ARBs within the liposomes, even when in the presence of serum. Without being bound by theory, it is believed that HPCD interacts with the ARB compound in a manner that affects the leakage of the ARB from the liposomes, perhaps by complexation.

In some examples, the CD (preferably HPCD) to phospholipid molar ratio is between 0.05 and 0.5. In some examples, the CD to phospholipid molar ratio is between 0.075 and 0.4, or 0.1 and 0.3. The CD to phospholipid molar ratio can be derived from the assumption that in a 5% liposomal volume the HPCD concentrations in the formulations is 7.5 mg/ml and 12.5 mg/ml for 15% and 25% HPCD containing formulations, respectively (when only liposomal HPCD remains after dialysis).

In some examples, the ARB to CD molar ratio is determined and defines the liposomal formulations. In some examples, the ARB to CD molar ratio is between 0.5 and 2.0, at times, between 0.6 and 1.9, at times between 0.7 and 1.5. Similar to the above, the ARB to CD molar ratio can be derived from the assumption that in 5% liposomal volume comprise HPCD concentrations of 7.5 mg/ml and 12.5 mg/ml for 15% and 25% formulations, respectively.

When referring to the inhalable liposomes, and in accordance with some examples, the lipid membrane thereof comprises or consists of dipalmitoyl phosphatidylcholine (DPPC) and cholesterol at a DPPC:Cholesterol molar ratio of from 100/0 to 55/45.

One preferred example concerns liposomes as described in ALIS (Arikayc) which consists of dipalmitoyl phosphatidylcholine (DPPC) and cholesterol at a weight ratio of 2:1 and molar ratio of 1:1.

The liposomes can be of any form or size.

In some examples, the liposomes are multilamellar or oligolamellar vesicles.

In some examples, the liposomes are multivesicular vesicles.

In some other examples, the liposomes are unilamellar vesicles.

The liposomes can be small, medium, large or even giant. When referring to small liposomes it is to be understood as having an average size in the range of between about 20 nm-100 nm; when referring to medium sized liposomes, it is to be understood as having an average size in the range of between about 100 nm-200 nm; when referring to large liposomes, it is to be understood as having an average size above about 200 nm; and when referring to giant liposomes (typically giant unilamellar or multivesicular vesicles), it is to be understood as referring to those being larger than 1 μm.

In some examples, particularly when referring to the injectable liposome aspect, the liposomes are small unilamellar vesicles (SUV). In some examples, the injectable SUV have a size distribution of between 20 nm to 100 nm; at times, between 20 nm to 100 nm, further at times, between 40 nm to 100 nm or 50 to 100 nm.

In some examples, the injectable liposomes have an average size of between 60 to 90 nm; at times, between 70 nm to 80 nm; and at times, about 77±5.0 nm.

In some other examples, particularly when referring to the inhalable liposome aspect, the liposomes can have an average size below 600 nm. In some examples, the inhalable liposomes are unilamellar. As such, the inhalable liposomes can have a size below 100 nm, thus being SUV; or can have a size above 100 nm, thus being LUV. In some examples, the inhalable liposomes have an average size of between about 50 nm and 600 nm, at times, about 300±20 nm.

The liposomes are stable. In fact, it has been found that when within a physiologically acceptable medium, the liposomes encapsulating the ARBs were significantly stable under the storage conditions at 4° C. as well as in serum.

When referring to stability in the context disclosed herein it is to be understood that following storage (at 4° C.) for at least a month, no more than 20%, at times, no more than 10% of the ARB compound would be released to the storage medium compared to the initial loaded ARB. In some examples, the stability of the liposomes is characterized by the fact that no more than 10% of ARB is released during storage to the surrounding medium after at least 3 months storage at 4° C. In some examples, the stability of the liposomes is characterized by the fact that no more than 10% of ARB is released to the surrounding medium after at least 4 months, 5 months, 6 months, 7 months, 8 months, 9 months, 12 months, and even 24 months under storage at 4° C.

The stability is determined by one or both of chemical and physical stability under storage conditions (4° C., in buffer).

In this context, chemical stability may be examined, inter alia, by one or more of the following parameters:

a) Measurement of dispersion pH (pH meter);

b) phospholipid (PL) acyl-ester hydrolysis by determination of change in non-esterified (free) fatty acids (NEFA) released upon PL hydrolysis [Barenholz et. al. From Liposomes: a practical approach, $2^{nd}$ Edn., RRC New ed, IRL Press Oxford, 1997] or by thin layer chromatography (TLC) [Barenholz, Y. and Amsalem, S. In: Liposome Technology $2^{nd}$ Edn., G. Gregoriadis (Ed.) CRC Press, Boca Raton, 1993, vol. 1, pp: 527-616], of by HPLC methods.

Physical stability of the liposome may be examined, inter alia, by one or more of the following parameters:

a) liposome size distribution by dynamic light-scattering (DLS).

b) Level of free (non-associated/aggregated) component.

c) zeta potential.

d) % Loading of the drug.

The liposomes disclosed herein are stable by at least one of the above stability parameters.

The liposomes can be prepared according to the remote loading technique. The preparation of the injectable liposomes can be using the calcium acetate (CA) gradient method [Clerc S, Barenholz Y. 1995. Loading of amphipathic weak acids into liposomes in response to transmembrane calcium acetate gradients. Biochim Biophys Acta 1240:257-265].

For example, lipids in a desired molar ratio, e.g. 55:40:5 HSPC:cholesterol:mPEG DSPE, are mechanically hydrated by stirring at 65° C. with 200 mM calcium acetate pH 5.5, at a weight ratio of 1:9. The liposomal dispersion is downsized by stepwise extrusion. Liposomes are then dialyzed using a regenerated cellulose membrane, against a 10% sucrose solution. In the case of HPCD-containing liposomes, lipids are hydrated by 200 mM calcium acetate pH 5.5 containing the desired % (w/w) HPCD.

Remote loading is then performed by incubating at 65° C. for 3 min-30 min a solution or dispersion of the ARBs with the liposome dispersion at a volume ratio of that will result in a desired ARB/phospholipid molar ratio, preferably ARB/phospholipid molar ratio of 0.02-1.0 as described above.

In some examples, the ARB/phospholipid molar ratio is at most 1.0; at times, the ARB/phospholipid molar ratio is at most 0.09; at times, the ARB/phospholipid molar ratio is at most 0.08; at times, the ARB/phospholipid molar ratio is at most 0.07; at times, the ARB/phospholipid molar ratio is at least 0.06.

ARB loading solutions or dispersions are prepared in 200 mM phosphate buffer pH 6.3.

When referring to the inhalable liposome aspect, it is to be understood to encompass liposomes that are of particular use for local delivery of the ARB to the respiratory tract. In other words, the inhalable liposomes are suitable for local delivery. It has been envisaged that the inhalable liposomes, being suitable for local delivery, provide their effect without causing a reduction in mean blood pressure in said subject of more than 50% as compared to inhalation of the same amount of ARB in free form, this being similar to the low or lack of effect of the injectable liposomes on the MBP.

Thus, the inhalable liposomes disclosed herein are particularly useful for treating a condition along the respiratory tract, such as infections.

In some examples, the inhalable liposomes disclosed herein are suitable for treating viral infection, such as that caused by coronavirus. One condition of interest is the Acute Respiratory Distress Syndrome (ARDS).

In the case of ARDS, a major inflammation occurs that results in a process called Extravasation through Leaky Vasculature (ELVIS) and therefore the infected lungs should get high dose of liposomes. The IC50 of valsartan and candesartan to AT1 receptor are 60 and 3 nM, respectively, corresponding to 30 and 1.3 ng/ml, respectively. Assuming tidal volume (volume that enters and leaves with each breath, from a normal quiet inspiration to a normal quiet expiration) of 0.5 L, 15 μg and 0.65 μg should be administered. These amounts can be achieved with the liposomal concentrations obtained according to the inhalable liposomes disclosed herein.

In the case of corona treatment, the two liposomal formulations (the injectable liposomes and inhalable liposomes allow to approach the lungs from inside (blood) and outside (inhalation). The use of the inhalable liposomes for anti-viral treatment is further discussed below.

Detailed description of the preparation of these liposomes for inhalation may be found in Shirley, M., Amikacin Liposome Inhalation Suspension: A Review in Mycobacterium avium Complex Lung Disease. Drugs, 2019. 79(5): p. 555-562 incorporated herein by reference.

The present disclosure also provides a formulation for use in a method of treatment, the formulation comprises the liposomes encapsulating at least one ARB compound as described herein and a physiologically acceptable carrier.

In the context of the present invention, a physiologically acceptable carrier denotes any carrier that is useful in preparing a pharmaceutical formulation that is generally safe, non-toxic and neither biologically nor otherwise undesirable.

In some examples, the formulation comprises a physiologically acceptable carrier suitable for administration by injection or infusion. This is of particular relevance to the injectable liposomes aspect disclosed herein. In some examples, the administration is by any one of intravenous (i.v.), intramuscular (i.m.), intra-peritoneal (i.p.), and subcutaneous (s.c.) injection.

In some other examples, the formulation comprises a physiologically acceptable carrier suitable for administration by inhalation. To this end, the liposomes may be in suspension or a priori lyophilized into a dry powder.

The formulation can be used for treating any conditions for which the delivery of at least one ARB compounds can provide a therapeutic benefit.

As appreciated, ARBs are highly selective for the AT1 receptor and block the deleterious effects of Ang II, such as vasoconstriction, aldosterone release, retention of sodium and water, sympathetic nerve activation and cell proliferation.

In addition to their known and clinically used activity as anti-hypertensive drugs, ARB's were shown in several prospective and retrospective studies to improve cancer treatment. In the level of the tumor microenvironment, ARB's were found to affect Cancer-associated fibroblasts (CAFs). CAF's can either inhibit or enable antitumor immunity, suggesting that they may be reprogrammed between these states. ARB's can reprogram CAFs to a quiescent state. In addition, ARB's may reduce immunosuppression and improve cancer immunotherapy efficacy.

In addition, ARB potentially has an effect on angiotensin-converting enzyme 2 (ACE2) receptor. ACE2 has recently gained a major attention being the binding site for the SARS-CoV-2, the strain implicated in the current COVID-19 epidemic and the activity thereof. Specifically, it has been demonstrated that the binding of the coronavirus spike protein to ACE2, its cellular binding site, leads to ACE2 downregulation, which in turn results in excessive production of angiotensin by the related enzyme ACE, while less ACE2 is capable of converting it to the vasodilator heptapeptide angiotensin. This in turn contributes to lung injury, as angiotensin II binding to AT receptor results in increased pulmonary vascular permeability, thereby mediating increased lung pathology.

Thus, when using liposomes encapsulating ARB's against viral infection, two complementary mechanisms occur: blocking the excessive angiotensin-mediated AT receptor activation caused by the viral infection, as well as upregulating ACE2, thereby reducing angiotensin production by ACE and increasing the production of the vasodilator angiotensin. Thus, ARB's administration is therapeutic approach to the COVID-19 infection.

In view of the above, and in accordance with some examples, the liposomes disclosed herein of the formulations comprising them are for use in treatment of cancer, i.e. as an anti-cancer treatment. The anti-cancer treatment is particularly relevant to the injectable liposomes aspect of the present disclosure.

In accordance with some other examples, the liposomes disclosed herein of the formulations comprising them are for use in treatment of viral infection, i.e. as an anti-viral treatment. The anti-viral treatment is particularly relevant to the inhalable liposomes aspect of the present disclosure.

The present disclosure also provides a method of treatment, the method comprises administering to a subject in need of an ARB, liposomes encapsulating at least one ARB, the liposomes being as defined herein and the amount of the at least one ARB being effective to achieve the desired treatment.

The amount of the at least one ARB is designed to be sufficient to provide a therapeutic effect upon administration (systemic or local) of the at least one ARB to a subject, yet without exhibiting a significant effect on the treated subject's mean blood pressure.

An amount sufficient or effective to achieve a desired therapeutic effect upon administration is to be understood as including at least one therapeutic effect known to be achieved by or associated with ARB, other than its potential effect on blood pressure.

In the context of the present disclosure when referring to an effect other than an effect on blood pressure it is to be understood that the liposomes disclosed herein, either being those administrable by injection or those being administrable by inhalation; exhibit their prime effect on a medical condition that is other than an effect involving reduction of blood pressure.

In some examples, the effect on blood pressure, if exhibited, is less than 50% as compared to the effect of the same dose of ARB in free form at the same mode of administration (e.g. injection, inhalation). At times, the effect is less than 40% as compared to the effect of the same amount of ARB in free form at the same mode of administration (e.g. injection, inhalation). Further, at times, the effect is less than 30% as compared to the effect of the same amount of ARB in free form at the same mode of administration (e.g. injection, inhalation). Yet, at times, the effect is less than 20% as compared to the effect of the same amount of ARB in free form at the same mode of administration (e.g. injection, inhalation). Further, at times, the effect is less than 10% as compared to the effect of the same amount of ARB in free form at the same mode of administration (e.g. injection, inhalation).

In other words, the effect of the liposomes upon administration, be it by injection or by inhalation, to a subject in need of the ARB effect for treating a condition, is without causing a reduction in mean blood pressure in the subject of more than 50% as compared to the same amount of ARB in free form, provided to the subject by the same mode of administration; at times of more than 40%, further at times, of more than 30%, or even of more than 20%, as compared to the same amount of ARB in free form, delivered by the same mode of administration.

Thus, for example, when referring to injection of the liposomes, e.g. for treating cancer, the effect of the liposomes on the cancerous cells is exhibited, while there is less than 50% effect, at times, less than 40%, less than 30%, less than 20%, or even less than 10% on the subject's blood pressure, as compared to the effect of the same drug when treated without the liposomes. The non-limiting examples presented below support the above as they show that the liposomal ARB had no effect on MBP compared to reduction from 105 to 70 mmHg of the free drug.

In some examples, the effect on blood pressure, if exhibited, is considered to be statistically insignificant (medically insignificant).

The amount of ARB to be delivered by the pharmaceutical formulation depends on various parameters as known to those skilled in the art and can be determined based on appropriately designed clinical trials (dose range studies) and the person versed in the art will know how to properly conduct such trials in order to determine the effective amount. The amount depends, inter alia, on the type and severity of the disease to be treated and the treatment regime (mode of systemic administration), gender and/or age and/or weight of the treated subject, etc.

In view of the above, in the context of the present disclosure, when referring to treatment by the liposomes disclosed herein, it is to be understood as encompassing ameliorating undesired symptoms associated with a disease, preventing the manifestation of such symptoms before they occur, slowing down the progression of a disease, slowing down the deterioration of symptoms, enhancing the onset of remission period of a disease, slowing down irreversible damage caused in progressive chronic stages of a disease, delaying onset of progressive stages, lessening severity or cure a disease, improving survival rate or more rapid recovery from a disease, preventing the disease from occurring, or a combination of two or more of the above.

The invention will now be described by way of non-limiting examples.

DESCRIPTION OF NON-LIMITING EXAMPLES

EXAMPLE 1

Preparation of Liposomal Formulations

Materials and methods

Materials

The materials used for the preparation of the formulations are found in Table 1.

TABLE 1

Materials used for formulation preparations.

| Material | Details |
|---|---|
| Valsartan | Assia LTD, Israel. CTRL no. 289590007 |
| Candesartan | Angene International Limited, Batch no. 024-004-43 |
| Dowex 1 × 8-200 anion exchanger | Sigma |
| LipidMix | Lipoid, a mixture of hydrogenated soy - phosphatidylcholine (HSPC), Cholesterol and N-(carbonyl-methoxypolyethylene glycol 2000)-1,2-distearoyl-sn-glycero3-phosphoethanolamine sodium salt (MPEG-DSPE) at a weight ratio of 3:1:1. |
| Hydroxypropyl-beta-cyclodextrin (HPCD) | Roquette, Lestrem, France. |
| Calcium acetate | Merck, Cat no. 1.02052.1000, Lot no. K44423152332 |
| Monobasic sodium phosphate | Sigma |
| Disodium phosphate dehydrate | Sigma |
| Adult bovine serum | Biological Industries (Beit Haemek, Israel) |
| Sepharose CL-4B | GE Healthcare (Little Chalfont, UK) |

Methods

Preparation of Calcium Acetate Liposomes

Nanoliposomes were prepared by mechanically hydrating LipidMix containing HSPC:Cholesterol:mPEG DSPE at a weight ratio of a 3:1:1, respectively, with 200 mM calcium acetate pH 5.5 at 65° C. (hereinafter "calcium acetate liposomes"). In case of liposomes containing HPCD, the hydrating solution contained in addition 15% (w/w) or 25% (w/w) HPCD. The liposomal dispersions were downsized by stepwise extrusion by the Northern Lipids extruder (Burnaby) using polycarbonate filter membranes and dialyzed against a 10% sucrose solution.

Liposomes Size

Particle size was determined using the dynamic light scattering method, performed with a Zetasizer Nano Series ZEN3600F (Malvern Instruments, Malvern, UK). Nanoliposome size was in the range of 73-83 nm and PDI<0.05.

Valsartan Analytical Method

Valsartan analytical method (HPLC) was implemented based on USP method.

The chromatographic conditions are described below:

Mobile phase—Acetonitrile: DDW: glacial acetic acid at a volumetric ratio of 50:50:0.1

Column—Phenomemex C18, 150×4.6 mm

Detector—UV 230 nm, 25 nm

Flow rate—1 ml/min

Injection vol.—20 µl

Column temp—30° C.

Candesartan Analytical Method

Candesartan analytical method (HPLC) was implemented based on USP method.

The chromatographic conditions are described below:

Mobile phase—Acetonitrile: DDW: Trifluoracetic acid at a volumetric ratio of 550:450:1

Column—Phenomemex C8, 150×4.6 mm

Detector—UV 254 nm, 282 nm

Flow rate—1 ml/min

Injection vol.—20 μl

Column temp—30° C.

Results

Valsartan

Valsartan Loading

The chemical structure of Valsartan is illustrated in Formula I below.

Formula I

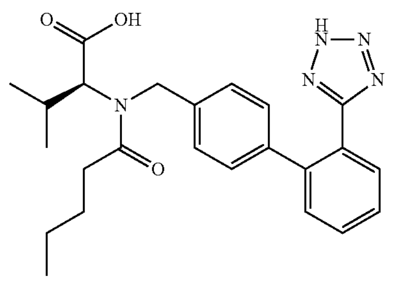

Valsartan has one carboxylic group that is ionized at relevant pH (3.2-8.8) and over this pH range it is in equilibrium with the unionized species. Valsartan was therefore loaded into calcium acetate liposomes (HSPC:Cholesterol:$^{2000}$MPEG-DSPE, 3:1:1). As these liposomes are required to be highly stable in the circulation, loading was tested also for liposomes exhibiting trans-membrane gradient of calcium acetate using liposomes containing in their intra-liposome aqueous phase either 15% HPCD or 25% HPCD. HPCD prevent a fast drug release in serum and allow slow and controlled drug release [J. D. Martin, H. Cabral, T. Stylianopoulos, R. K. Jain, Improving cancer immunotherapy using nanomedicines: progress, opportunities and challenges, Nat. Rev. Clin. Oncol. 17 (2020) 251-266].

Loading of valsartan was performed by solubilizing the drug in phosphate buffer 200 mM pH 6.3 and adding it to the liposomal dispersion at 65° C. Loading efficiency was tested using Dowex anion exchanger which previously was shown to absorb efficiently free valsartan but not liposomal drug.

Table 2A provides the liposomal valsartan concentrations (mg/ml) and Table 2B provides liposomal valsartan D/L molar ratio obtained at three different loading conditions:

Condition A—Addition of all drug at once followed by 10 minutes incubation;

Condition B—Addition of all drug at once followed by 3 minutes incubation;

Condition C—Addition of the drug in portions.

All liposomes are calcium acetate liposomes, with or without (w/o) HPCD.

TABLE 2A

Liposomal valsartan concentrations (mg/ml) obtained at the different conditions

| D/L | Condition A | | Condition B | Condition C | |
|---|---|---|---|---|---|
| molar ratio | w/o HPCD | With 15% HPCD | with 25% HPCD | w/o HPCD | with 15% HPCD |
| 0.1 | 2.8 | 2.3 | 2.8 | 2.8 | 2.5 |
| 0.2 | 2.2 | 2.9 | 3.8 | 3.7 | 3.3 |
| 0.3 | 0.5 | 1.7 | 3.5 | 2.3 | 2.5 |
| 0.4 | 0.5 | 0.8 | 2.7 | 1.5 | 1.8 |

TABLE 2B

Liposomal valsartan D/L molar ratio with or without (w/o) HPCD

| D/L | Condition A | | Condition B | Condition C | |
|---|---|---|---|---|---|
| molar ratio | w/o HPCD | With 15% HPCD | with 25% HPCD | w/o HPCD | with 15% HPCD |
| 0.1 | 0.11 | 0.11 | 0.13 | 0.11 | 0.12 |
| 0.2 | 0.11 | 0.16 | 0.21 | 0.18 | 0.19 |
| 0.3 | 0.03 | 0.12 | 0.23 | 0.14 | 0.17 |
| 0.4 | 0.03 | 0.06 | 0.21 | 0.10 | 0.14 |

FIG. 1 presents % loading of valsartan into these liposomes following 10 min of incubation at different D/L molar ratios.

High loading of ~100% was obtained for D/L of 0.1. Loading efficiency decreased with the increase in D/L ratio and was sharper for liposomes exhibiting transmembrane calcium acetate gradient without intra-liposome HPCD.

Figure 2:
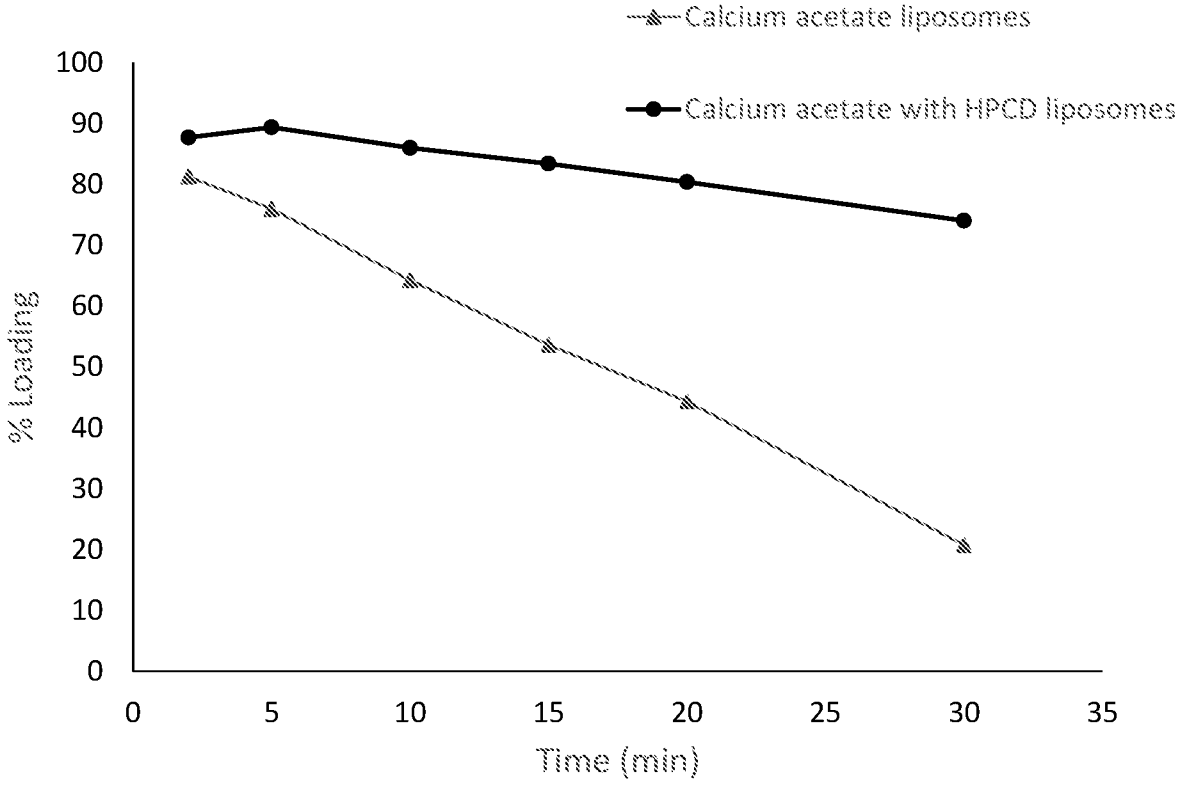
FIG. 2 is a graph showing kinetic of loading into liposomes with 15% HPCD or without HPCD at D/L of 0.2.

FIG. 2 presents the kinetic of loading into liposomes at D/L of 0.2 with 15% HPCD or without HPCD. For calcium acetate liposomes, loading was highest when incubation terminated after 2 min (81%) and decreased over time to 8% for 30 min incubation time. For liposomes containing 15% HPCD, loading was found to be stable over the first 20 min ranging from 80-89%. Decrease was observed for 30 min incubation resulting in 74% loading.

In an effort to increase loading efficiency, the loading into the liposomes while adding the drug solution in portions was tested. In this test, incubation for 3 min was performed with valsartan at a D/L ratio of 0.1. Incubation at D/L of 0.2 was performed by additional drug solution added after 3 min and incubate for additional 2 min. For D/L of 0.3 and 0.4 fractions of drug were added as described for D/L of 0.2 by addition of more drug solution and incubation for additional 2 min (total incubation time for D/L of 0.4 was 9 min). Addition of the drug in portions increased substantially the loading compared to that obtained after 10 min of incubation of all drug at once as presented in FIG. 3.

Figure 3:
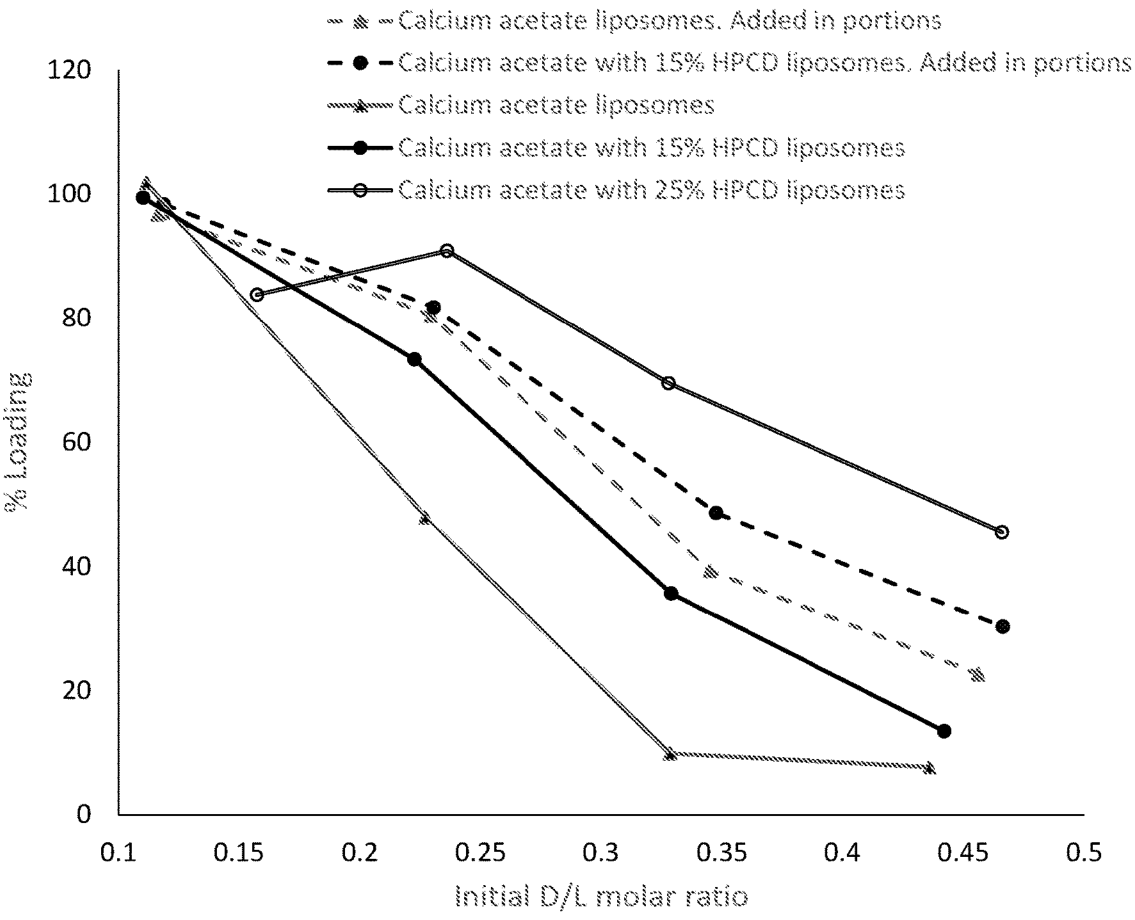
FIG. 3 is a graph showing the Loading efficiency of valsartan into liposomes with or without HPCD (15 and 25%), as a function of D/L molar ratio; with drug addition in one fraction vs addition in portions.

Liposomes containing 25% HPCD in their intra-liposome aqueous phase were also loaded with valsartan. The doubled black line in FIG. 3 presents these results. Loading was performed following incubation for 3 min in one portion. Loading efficiency obtained was the highest compared to all other conditions tested.

Valsartan Release

Release in Dextrose

The release from valsartan liposomes was first tested following dilution in dextrose while incubated at 37° C. Valsartan loaded liposomes with and without HPCD were used for the test. The liposomes used were those loaded with valsartan at a D/L molar ratio of 0.1.

Figure 4:
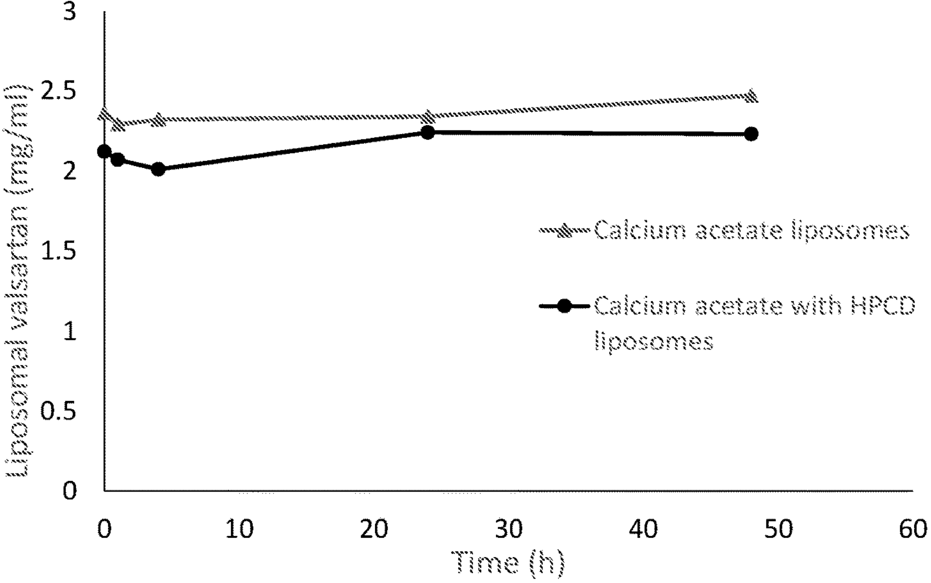
FIG. 4 is a graph showing liposomal valsartan concentrations following 48 h incubation at 37° C.
Figure 5:
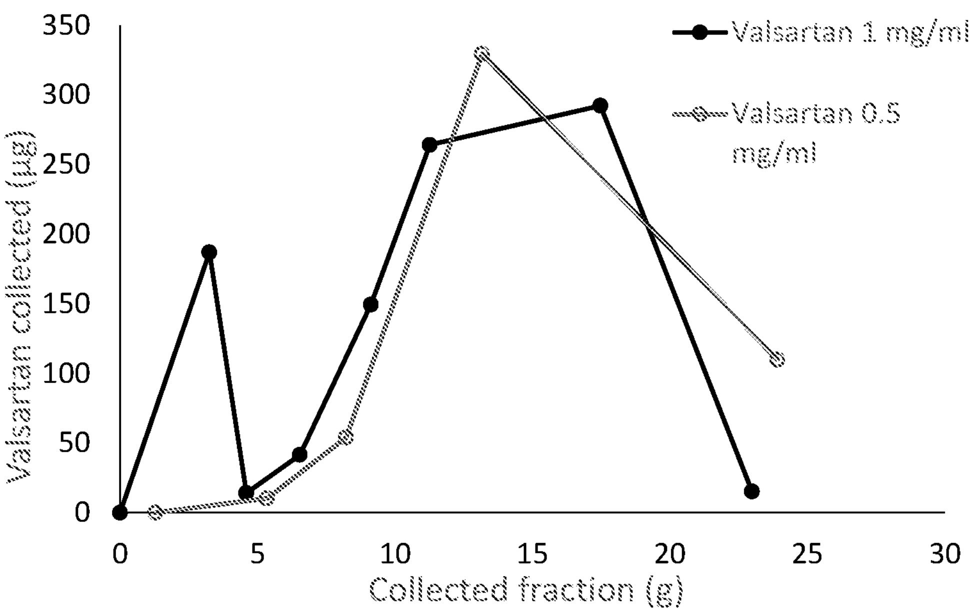
FIG. 5 is a graph showing free valsartan application on Sepharose column (1 mg/ml vs 0.5 mg/ml).

Liposomes were diluted 10-fold in dextrose and placed at 37° C. incubator. Following 1, 4, 24 and 48 h, samples were taken from the incubation and the liposomal fraction was separated using Dowex ion exchanger. No release from the liposomes was obtained over 48 h of incubation as described in FIG. 4.

Release in 50% Serum

Separation of free and liposomal fractions of the drug in the presence of serum require separation by size exclusion chromatography (SEC). For this purpose, Sepharose CL4B was used. The separation method require adaptation for each of the mixtures of free drug and liposomal drug. Free valsartan at 0.5 mg/ml concentration was tested for its elution profile by the column and was eluted only in late fractions allowing separation of free valsartan from liposomal valsartan that is eluted in early fractions.

Figure 6:
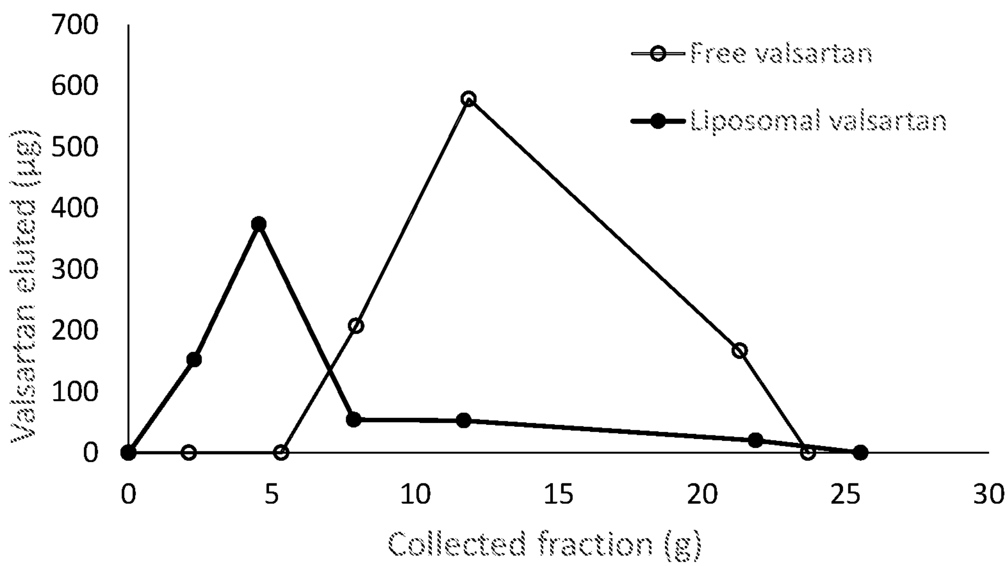
FIG. 6 is a graph showing free vs. liposomal valsartan elution on Sepharose column.
Figure 7:
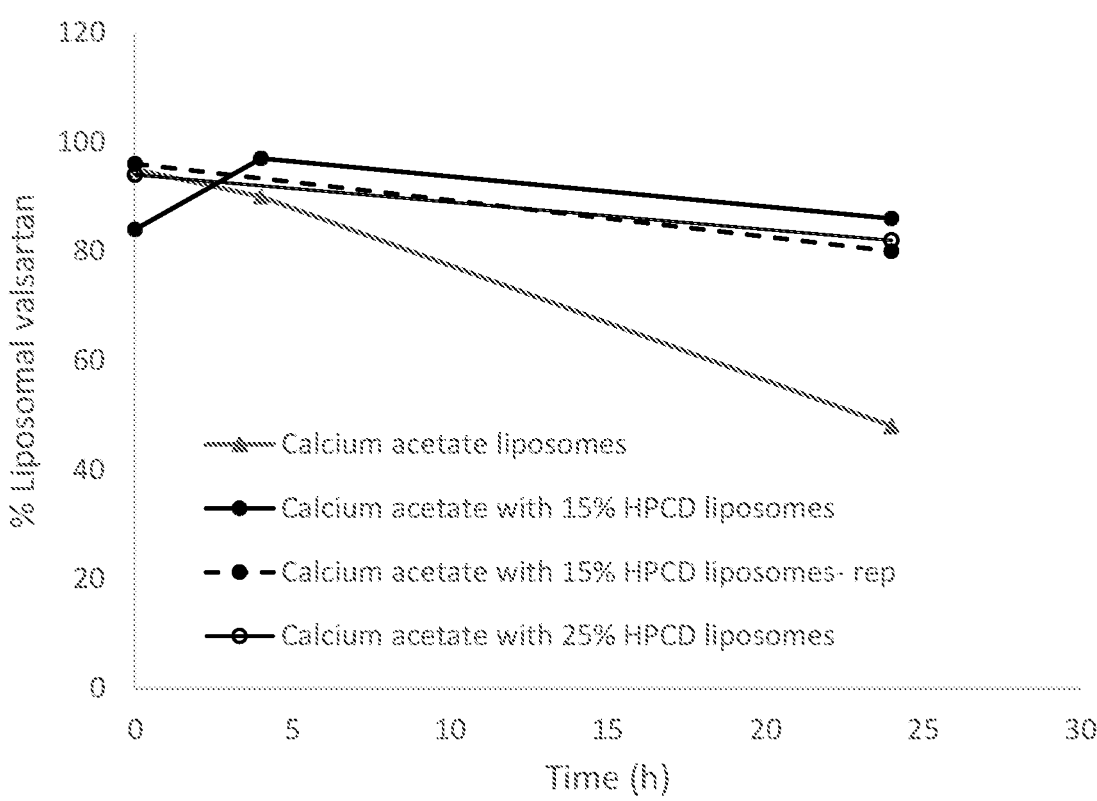
FIG. 7 is a graph showing percent liposomal valsartan over 24 h of incubation at 37° C. in the presence of 50% serum.

The elution profile of free valsartan vs liposomal valsartan as described in FIG. 6 was also examined. Having the method suitable for the separation of liposomal and free valsartan allowed to perform the release test of valsartan from liposomes in the presence of serum. FIG. 7 presents these results.

Valsartan was found to be slowly released from calcium acetate liposomes and after 24 h, only 45% of the drug remained liposomal. The release from liposomes exhibiting trans-membrane calcium acetate gradient and HPCD was much slower with 87% of the drug retained in the liposomes after 24 h. This value is similar to % liposomal found at t=0 (84%) and lower than % liposomal found after 4 h (96%). This assay was repeated and showed similar results of 80-86% liposomal valsartan after 24 h of incubation. The release of valsartan from liposomes containing 25% HPCD (D/L 0.2) was similar to 15% HPCD showing 82% liposomal valsartan after 24 h of incubation.

Loading Stability Upon Storage

Valsartan liposomes with and without HPCD at different D/L molar ratios that were stored for 5 months at 4° C. were tested for their loaded valsartan content as summarized in Table 3. In Table 3, The formulations are either based on intraliposomal calcium acetate alone or calcium acetate with 15% HPCD formulations loaded with increased ARB/phospholipid (D/L) molar ratios in the initial incubation.

Loading was found to be stable over time and even increased over the storage period, as can be expected from remote loaded liposomes.

TABLE 3

Loading stability of valsartan liposomal formulations stored at 4° C.

| Form* | D/L molar ratio** | Lip. Conc. at t = 5M (mg/ml) | Lip. Conc. at t = 15M (mg/ml) | % at t = 0 | % at t = 5M | % at t = 15M |
|---|---|---|---|---|---|---|
| Calcium acetate liposomes | | | | | | |
| AH3-5(9) | 0.1 | 2.7 | ND | 102 | 97 | ND |
| AH3-5(10) | 0.2 | 3.5 | 3.7 | 48 | 76 | 89.3 |
| AH3-5(3) | 0.3 | 2.1 | 2.5 | 9.9 | 39 | 51.0 |
| AH3-5(4) | 0.4 | 1.4 | 2.0 | 7.7 | 22 | 36.5 |
| Calcium acetate-15% HPCD liposomes | | | | | | |
| AH3-5(5) | 0.1 | 2.5 | ND | 99 | 108 | ND |
| AH3-5(6) | 0.2 | 3.2 | 3.5 | 73 | 85 | 90.4 |
| AH3-5(8) | 0.4 | 1.9 | 2.1 | 13 | 34 | 39.7 |

*internal reference
**in initial incubation
ND = not determined

Liposomal Valsartan Activity on Mice Blood Pressure

The development of liposomal ARB's aimed at delivering the drugs to the tumor and exert their activity there while avoiding the systemic effect of the drug on blood pressure. The in vivo study therefore tested the effect of free valsartan (at 25 mg/kg dose) on mouse mean blood pressure (MBP). MBP was measured using CODA monitor device allowing measurement of blood pressure in mouse tail.

Four mice were tested before drug administration and 2, 24 and 48 h after drug administration. For each mouse, at least 3 measurements (and up to 10) were recorded for each time point.

Figure 8:
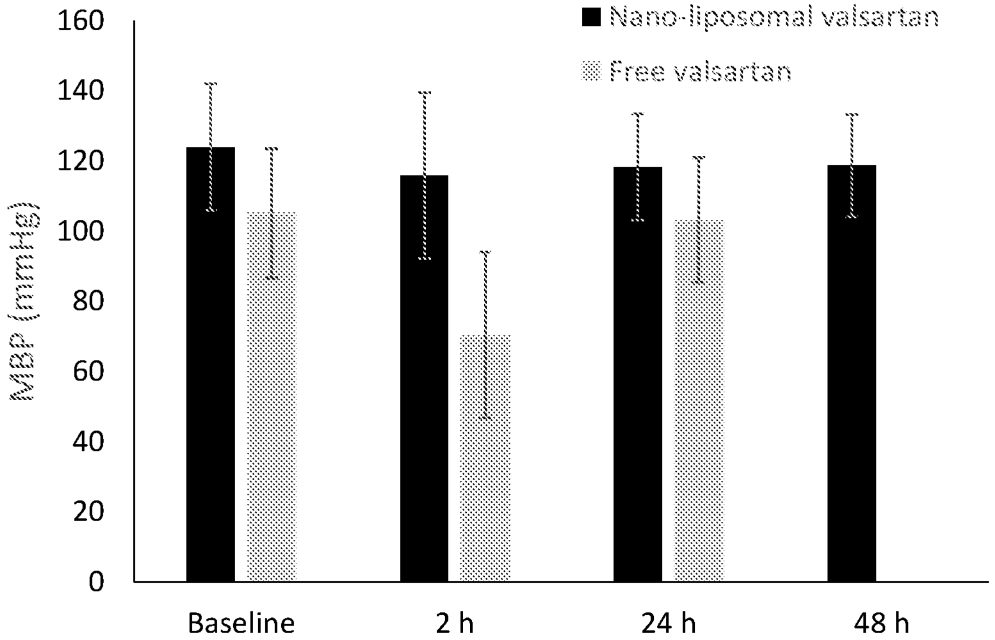
FIG. 8 is a graph showing mouse blood pressure after free valsartan or liposomal valsartan (25 mg/kg) administration as determined using CODA monitor device.

FIG. 8 presents the results obtained. Free valsartan resulted in lowering MBP in ~35 units 2 h after administration. MBP returned to baseline at t=24 h. Liposomal valsartan (15% HPCD formulation) at the same dose showed no effect on MBP over the time points tested.

Candesartan

Candesartan Loading

Candesartan chemical structure is described in Formula II below.

Formula II

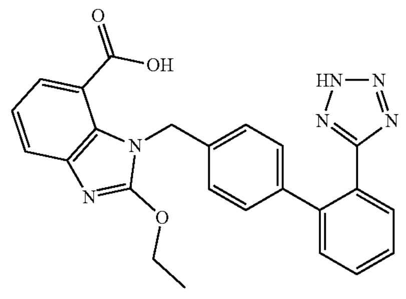

Candesartan has one carboxylic group that is ionized at relevant pH (1.6-8.8) and over this pH range it is in equilibrium with the unionized species (similar to valsartan). Candesartan was therefore loaded into liposomes exhibiting trans membrane calcium acetate gradient in liposomes having or lacking HPCD in their intra-liposome aqueous phase as described previously for valsartan.

Candesartan solubility is very limited (much lower than of valsartan) as previously described and has the highest affinity for AT1 receptor [Bhuiyan, M. A.; Shahriar, M.; Nagatomo, T. Binding Affinity of Candesartan, Losartan, Telmisartan and Valsartan with Angiotensin II Receptor 1 Subtype. Bangladesh Pharm. J. 2013, 16, 10-14, doi: 10.3329/bpj.v16i1.14484].

Therefore, candesartan was dispersed in phosphate buffer pH 6.3 to a concentration of 10 mg/ml and this dispersion was used for loading. As these liposomes are required to be highly stable in the circulation, loading was tested also for liposomes exhibiting trans-membrane calcium acetate containing also 15% and 25% HPCD in their intraliposomal aqueous phase, which was previously found to add to the stability in serum of Nano-liposomes.

Loading of candesartan into liposomes was performed at 65° C. and tested over time of 5 to 60 min incubation. Loading was performed from a dispersion at a molar D/L ratio of 0.4. After loading, the obtained liposomes were centrifuged and the total drug concentration after centrifugation was measured in the upper phase. The D/L molar ratio after centrifugation (excluding the precipitate) was 0.24 and 0.28 for liposomes lacking HPCD and liposomes including HPCD in their intra-liposome aqueous phase, respectively.

Figure 9:
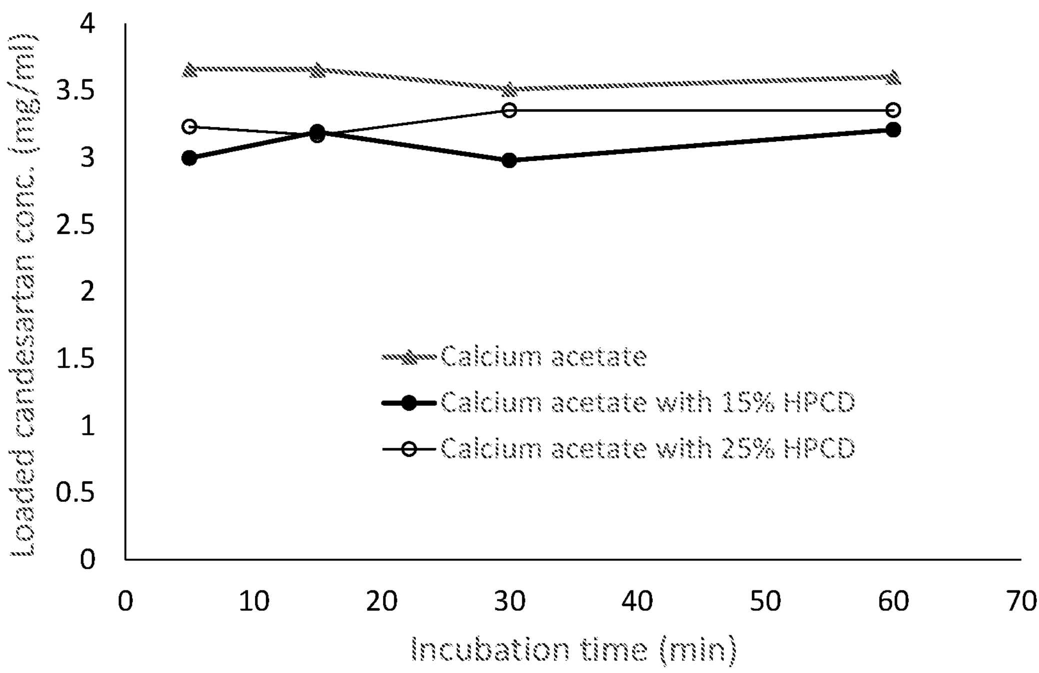
FIG. 9 is a graph showing loaded candesartan concentrations over incubation time.

FIG. 9 presents the loaded concentrations over the incubation time.

Figure 10:
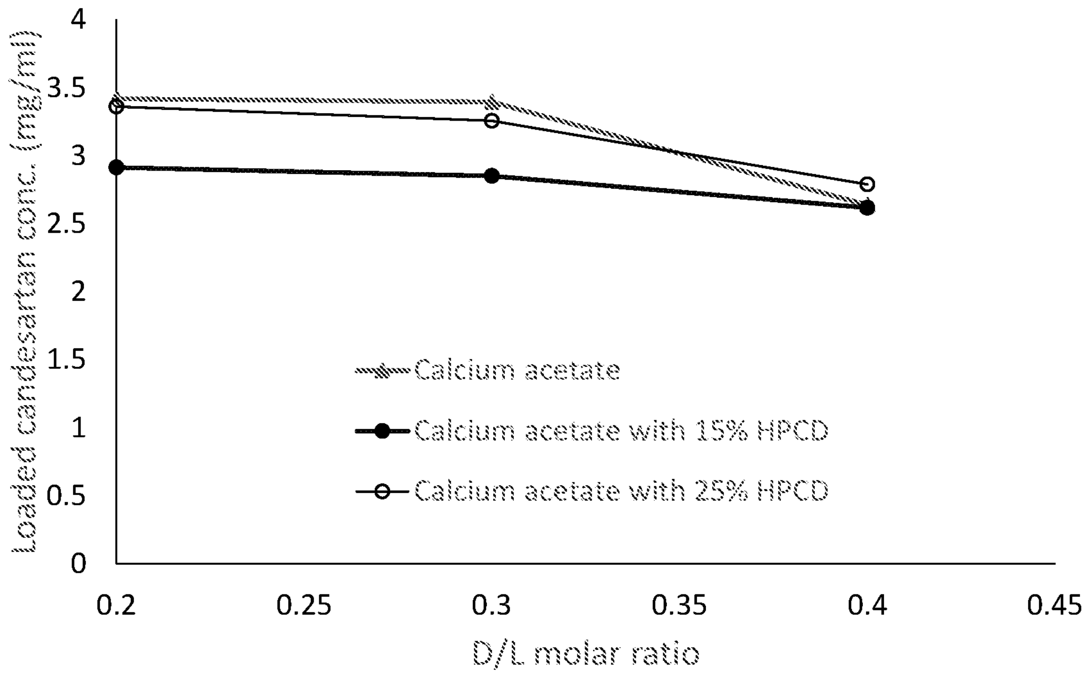
FIG. 10 is a graph showing loaded candesartan concentrations over different D/L ratios after 15 min incubation time.

FIG. 10 presents the loaded concentrations over initial D/L molar ratios tested (0.2-0.4). Loaded candesartan concentrations were in the range of 2.6-3.7 mg/ml.

Candesartan Release

Release in Saline

Figure 11:
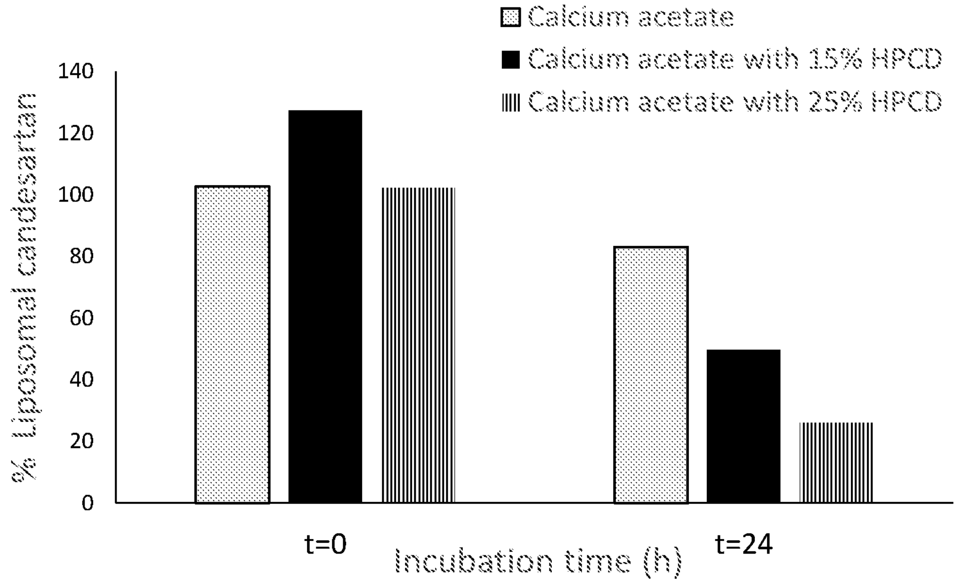
FIG. 11 is a graph showing percent liposomal candesartan following 24 h incubation in saline at 37° C.

Liposomes containing calcium acetate only, or with 15% or 25% HPCD loaded with candesartan were tested for their release following 20-fold dilution in saline at 37° C. The results obtained are described in FIG. 11. The surprising results were that candesartan was released from the liposomes over time and the release increased with the increase in the intra-liposome HPCD content.

Release in 50% Serum

Liposomal candesartan formulations exhibiting trans-membrane calcium acetate without intra-liposome HPCD and with 25% intra-liposome HPCD were diluted 15-fold with 50% serum. At t=0 and t=24 h samples were loaded on Sepharose column to separate between free and liposomal candesartan. The results are described in FIG. 12.

Figure 12:
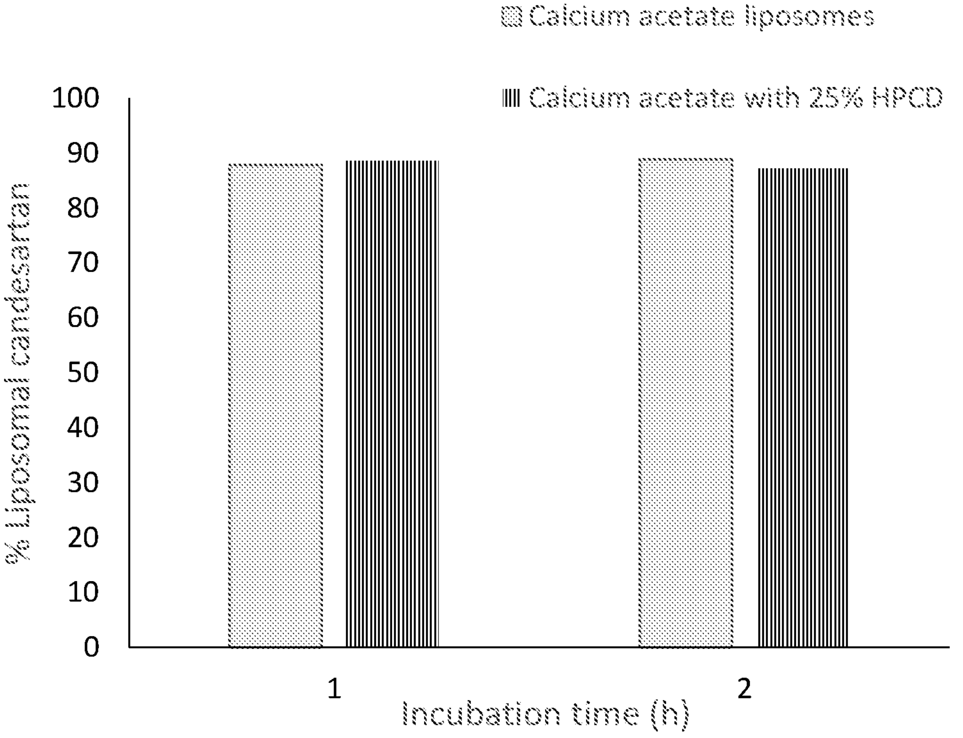
FIG. 12 is a graph showing liposomal candesartan following 24 h incubation in 50% serum at 37° C.

Specifically, FIG. 12 shows no decrease in liposomal candesartan content over 24 h of incubation for both formulations in the presence of serum.

These results were surprising because substantial release of candesartan was obtained in saline and was higher with increase in intraliposomal-HPCD concentrations. The fact that in serum, which in most cases triggers more rapid drug release as compared to saline, no release of candesartan was exhibited was unexpected.

EXAMPLE 2

In Vivo Studies—Valsartan and Candesartan

The therapeutic efficacy of the disclosed formulations is tested in 4T1 breast cancer model, in comparison to Doxil according to the following steps:

- The efficacy of treatment with Doxil alone or in combination with lead liposomal-ARB formulation is determined.
- Therapeutic efficacy in 4T1 breast cancer model compared to Immune Checkpoint Inhibition (ICI) treatment: The efficacy of ICI is determined As Is and in combination with the liposomal ARB formulation. The immune checkpoint cocktail that is used are anti-PD-1 (BioXcell) and anti-CTLA-4 (BioXcell).
- Therapeutic efficacy in human adenocarcinoma (HT29) model compared to ICI treatment: The efficacy of ICI is determined as is and in combination with the liposomal ARB formulation. The immune checkpoint cocktail that is used are anti-PD-1 (BioXcell) and anti-CTLA-4 (BioXcell).
- Pharmacokinetic studies including biodistribution in tumors, in diseased mice of lead formulation compared to free drug. Drug concentrations is determined in plasma and in the tumors.

EXAMPLE 3

Inhalable Liposomal Valsartan and Candesartan for Treating Coronavirus

Inhaled liposomal formulation for treating Acute Respiratory Distress Syndrome (ARDS), including coronavirus complication is based on DPPC and cholesterol.

In the case of ARDS, a major inflammation occurs that results in a process called Extravasation through Leaky Vasculature (ELVIS) and therefore the infected lungs should get high dose of liposomes. The IC50 of valsartan and candesartan to AT1 receptor are 60 and 3 nM, respectively, corresponding to 30 and 1.3 ng/ml, respectively. Assuming tidal volume (volume that enters and leaves with each breath, from a normal quiet inspiration to a normal quiet expiration) of 0.5 L, 15 ug and 0.65 ug should be administered. These amounts can be achieved with the liposomal concentrations obtained.

Nano-liposomes for inhalation are prepared by the same remote loading method described above, using trans-membrane calcium acetate gradient.

The lipid composition for the inhaled formulation comprises dipalmitoyl phosphatidylcholine (DPPC) and cholesterol at a weight ratio of 2:1 and molar ratio of 1:1. Intra-liposome HPCD at the concentration range of 0 to 30 is used in order to achieve the desired control on rate of ARB release of the liposomes. The size of the inhaled liposomes is ~300 nm.

The invention claimed is:

1. Liposomes, comprising:

a lipid membrane comprising at least one liposome forming phospholipid and a sterol; and an intraliposomal aqueous compartment encapsulating at least one AT1 receptor blocker, ARB, and a pH-dependent ionizable anion;

wherein:

the at least one ARB is selected from the group consisting of (2S)-3-methyl-2-[pentanoyl-[[4-[2-(2H-tetrazol-5-yl)phenyl]phenyl]methyl]amino]butanoic acid (Valsartan) of Formula I:

Formula I

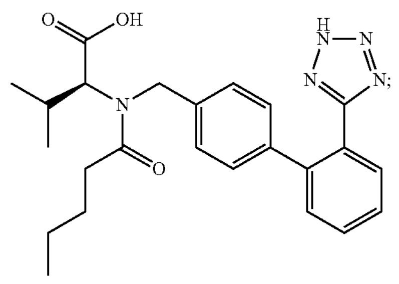

and 2-ethoxy-3-[[4-[2-(2H-tetrazol-5-yl)phenyl]phenyl]methyl]benzimidazole-4-carboxylic acid (Candesartan) of Formula II:

Formula II

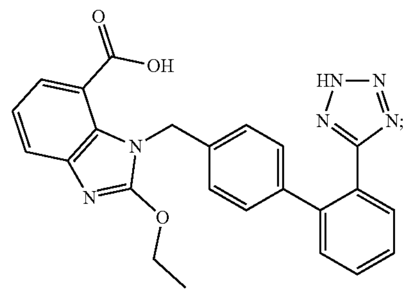

the at least one liposome forming phospholipid and the sterol are present at a weight ratio of between 3:1 and 2:1;

the liposomes have a molar ratio between the at least one ARB and the at least one phospholipid within the range of 0.02 to 1.0; and the at least one ARB is selected to provide, upon systemic administration of the liposomes, to a subject in need thereof, an effect, without causing a reduction in mean blood pressure of said subject of more than 50% as compared to systemic administration of the same amount of ARB in free form.

2. The liposomes of claim 1, wherein said lipid membrane comprises a lipopolymer.

3. The liposomes of claim 1, wherein said at least one liposome forming phospholipid comprises or consists of hydrogenated soy-phosphatidylcholine, HSPC other than a lipopolymer, if said lipopolymer is present in said lipid membrane.

4. The liposomes of claim 1, wherein said sterol includes cholesterol.

5. The liposomes of claim 1, wherein said intraliposomal aqueous compartment encapsulates at least one cyclodextrin, CD compound.

6. The liposomes of claim 5, wherein the at least one CD is 2-Hydroxypropyl-β-cyclodextrin, HPβCD.

7. The liposomes of claim 1, wherein said pH-dependent ionizable anion is acetate.

8. The liposomes of claim 2, comprising in the intraliposomal aqueous compartment said Valsartan, acetate as said pH-dependent ionizable anion and HPCD, wherein at least one of the following criteria is fulfilled:

a molar ratio between said Valsartan and said liposome forming phospholipid and said lipopolymer, if present, is between 0.02 and 1.0; or a molar ratio between said Valsartan and said HPCD being between 0.5 and 2.0.

9. The liposomes of claim 2, comprising in the intraliposomal aqueous compartment said Candesartan and acetate as said pH-dependent ionizable anion, wherein:

a molar ratio between said Candesartan and at least one liposome forming phospholipid and said lipopolymer, if present, is 0.02 and 1.0.

10. The liposomes of claim 1, wherein said lipid membrane comprises a combination of HSPC, cholesterol and N-(carbonyl-methoxypolyethylene glycol 2000)-1,2-distearoyl-sn-glycero-3-phosphoethanolamine ($^{2000}$PEG-DSPE).

11. The liposomes of claim 10, wherein said lipid membrane comprises a molar ratio of HSPC:cholesterol: $^{2000}$PEG-DSPE of 55:40:4.

12. The liposomes of claim 1, being small unilamellar vesicles, SUV.

13. A method of treatment, comprising:

administering to a subject in need of at least one ARB, the liposomes of claim 2.

14. The method of claim 13, wherein said liposomes comprise in the intraliposomal compartment said Valsartan, acetate as said pH-dependent ionizable anion and HPCD, wherein at least one of the following criteria is fulfilled:

a molar ratio between said Valsartan and said liposome forming phospholipid and said lipopolymer, if present, is between 0.02 and 1.0; or a molar ratio between said Valsartan and said HPCD being between 0.5 and 2.0.

15. The method of claim 13, wherein said liposomes comprise in the intraliposomal compartment said Candesartan and acetate as said pH-dependent ionizable anion, wherein at least one of the following criteria is fulfilled:

a molar ratio between said Candesartan and at least one liposome forming phospholipid and said lipopolymer, if present, is 0.02 and 1.0; or a molar ratio between said Candesartan and said HPCD being between 0.5 and 2.0.

16. Liposomes, comprising:

a lipid membrane comprising at least one liposome forming phospholipid and a sterol; and an intraliposomal aqueous compartment encapsulating at least one AT1 receptor blocker, ARB; said liposomes have an average size of between 50 nm and 600 nm, wherein said liposomes have an effect on a subject's respiratory tract, upon administration by inhalation, without causing a reduction in mean blood pressure in said subject of more than 50% as compared to inhalation of the same amount of ARB in free form.

17. The liposomes of claim 13, wherein said at least one liposome forming lipid comprises or consist of dipalmitoyl phosphatidylcholine, DPPC.

18. A method of treating a condition along a subject's respiratory tract, the method comprising:

administering to said subject, liposomes comprising:

a lipid membrane comprising at least one liposome forming phospholipid and a sterol; and an intraliposomal aqueous compartment encapsulating at least one AT1 receptor blocker, ARB;

wherein the at least one ARB is selected from the group consisting of (2S)-3-methyl-2-[pentanoyl-[[4-[2-(2H-tetrazol-5-yl)phenyl]phenyl]methyl]amino]butanoic acid (Valsartan) of Formula I:

Formula I

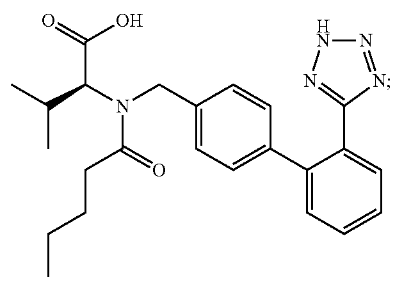

and 2-ethoxy-3-[[4-[2-(2H-tetrazol-5-yl)phenyl]phenyl]methyl]benzimidazole-4-carboxylic acid (Candesartan) of Formula II:

Formula II

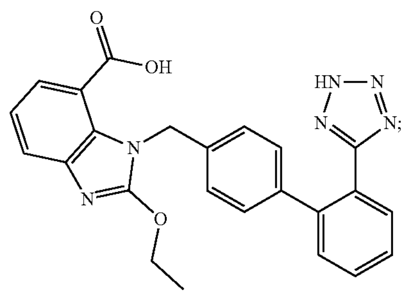

wherein said liposomes have an average size of between 50 nm and 600 nm; and wherein said method comprises selecting the ARB to provide, upon administration by inhalation of the liposomes, an effect on a subject's respiratory tract, without causing a reduction in mean blood pressure in said subject of more than 50% as compared to inhalation of the same amount of ARB in free form.

* * * * *